US006487441B1

(12) United States Patent
Swanson et al.

(10) Patent No.: US 6,487,441 B1
(45) Date of Patent: *Nov. 26, 2002

(54) SYSTEMS AND METHODS FOR ACQUIRING AND ANALYZING ELECTROGRAMS IN MYOCARDIAL TISSUE

(75) Inventors: David K. Swanson, Mountain View; James G. Whayne, Saratoga; Dorin Panescu, Sunnyvale, all of CA (US)

(73) Assignee: EP Technologies, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/717,798

(22) Filed: Nov. 20, 2000

Related U.S. Application Data

(60) Continuation of application No. 09/247,442, filed on Feb. 10, 1999, now Pat. No. 6,188,924, which is a continuation of application No. 08/955,328, filed on Oct. 21, 1997, now Pat. No. 5,954,662, which is a division of application No. 08/393,158, filed on Feb. 17, 1995, now Pat. No. 5,711,305.

(51) Int. Cl.[7] .............................. A61N 1/36; A61B 5/04
(52) U.S. Cl. ...................................................... 600/510
(58) Field of Search ........................ 600/509–511, 515, 600/518, 373–375, 547, 544, 546, 484; 607/9, 122; 128/901

(56) References Cited

U.S. PATENT DOCUMENTS

| 4,105,023 A | 8/1978 | Marchese et al. |
| 4,149,527 A | 4/1979 | Naylor et al. |
| 4,244,376 A | 1/1981 | Fisher et al. |
| 4,674,509 A | 6/1987 | DeCote, Jr. |
| 4,723,553 A | 2/1988 | Miwa et al. |
| 4,793,361 A | 12/1988 | DuFault |
| 4,868,773 A | 9/1989 | Coyle et al. |

(List continued on next page.)

FOREIGN PATENT DOCUMENTS

| WO | WO 94/21165 | 2/1994 |
| WO | WO 94/21168 | 3/1994 |
| WO | WO 94/16619 | 8/1994 |

OTHER PUBLICATIONS

Orthogonal Electrode Catheter Array for Mapping of Endocardial Focal Site of Ventricular Activation, Desai, J.M. et al., Pace vol. 14 pp. 557–576, Apr. 1991, Part 1.

Other Time and Frequency Domain Techniques, Panescu, Dorin, Biomedical Digital Signal Processing, Prentice Hall, pp. 216–228.

A Fast Pipelined Cordic–Based Adaptive Lattice Filter, Swanson et al., The American Journal of Cardiology vol. 71, Apr. 1, 1993.

Anisotropic Reentry, Wit et al., Cardiac Mapping, Futura Publishing Co., pp. 127–154.

(List continued on next page.)

Primary Examiner—Jeffrey R. Jastrzab
(74) Attorney, Agent, or Firm—Lyon & Lyon LLP

(57) ABSTRACT

Systems and methods for acquiring and analyzing electrograms in myocardial tissue are disclosed and described. One such method includes deploying a three dimensional, radially expanded array of multiple electrodes in operative association with a region of heart tissue; acquiring a sample of a cardiac event by placing the heart at a predetermined location using the multiple electrodes, while conditioning the multiple electrodes to sense paced electrograms occurring in the tissue region during pacing; and electronically comparing the sample to a template of a cardiac event of known diagnosis and generating an output based upon the comparison, whereby the output provides a diagnostic indicator based upon pacing.

17 Claims, 34 Drawing Sheets

U.S. PATENT DOCUMENTS

| | | | |
|---|---|---|---|
| 5,010,888 A | 4/1991 | Jadvar et al. | |
| 5,029,118 A | 7/1991 | Nakajima et al. | |
| 5,117,834 A | 6/1992 | Kroll et al. | 128/705 |
| 5,168,459 A | 12/1992 | Hiller | |
| 5,238,000 A | 8/1993 | Niwa | |
| 5,267,567 A | 12/1993 | Aung et al. | |
| 5,273,049 A | 12/1993 | Steinhaus et al. | |
| 5,311,873 A | 5/1994 | Savard et al. | |
| 5,311,874 A | 5/1994 | Baumann et al. | |
| 5,323,781 A | 6/1994 | Ideker et al. | |
| 5,324,284 A | 6/1994 | Imran | |
| 5,391,199 A | 2/1995 | Ben-Haim | |
| 5,405,375 A | 4/1995 | Ayers et al. | |
| 5,409,000 A | 4/1995 | Imran | |
| 5,409,007 A | 4/1995 | Saunders et al. | |
| 5,411,025 A | 5/1995 | Webster, Jr. | |
| 5,413,105 A | 5/1995 | Forestieri | |
| 5,415,166 A | 5/1995 | Imran | |
| 5,436,564 A | 7/1995 | Kreger et al. | |
| 5,447,519 A | 9/1995 | Peterson | |
| 5,450,846 A | 9/1995 | Goldreyer | |
| 5,454,370 A | 10/1995 | Avitall | |
| 5,476,495 A | 12/1995 | Kordis et al. | |
| 5,485,849 A | 1/1996 | Panescu et al. | |
| 5,487,391 A | 1/1996 | Panescu | |
| 5,595,183 A | 1/1997 | Swanson et al. | 600/510 |
| 5,711,305 A | 1/1998 | Swanson et al. | 600/510 |

OTHER PUBLICATIONS

Reentrant and Non–re–entrant Mechanisms Contribute to Arrhythmogenesis During Early Myocardial Ischemia: Results Using Three–Dimensional Mapping, Pogwizd et al., Circulation Research vol. 61 No. 3, Sep. 1987.

Identification of Reentry Circuit Sites During Catheter Mapping and Radio Frequency Ablation of Ventricular Tachycardia Late After Myocardial Infarction, Stevenson et al., Circulation, vol. 88, No. 4, Part 1, Oct. 1993, pp. 647–669.

Digital Signal Processing Chip Implementation for Detection and Analysis of Intracardiac Electrograms, Chiang et al., Pace vol. 17, Aug. 1994, pp. 1373–1379.

Induction of Ventricular Tachycardia During Programmed Electrical Stimulation: Analysis of Pacing Methods, Prystowsky et al., Circulation, vol. 73 (Supp. II) Feb. 1986, pp. II–32–II–38.

Catheter Ablation of Ventricular Tachycardia, Morady, Tachycardias: Mechanisms and Management, pp. 537–556.

Endocardial Actrivation Mapping and Endocardial Pacing–Mapping Using a Balloon Apparatus, Fann et al., The American Journal of Cardiology, vol. 55, Apr. 1, 1985, pp. 1076–1083.

Demonstration of the Presence of Slow Conduction During Sustained Ventricular Tachycardia in Man: Use of Transient Entrainment of the Tachycardia, Okumura et al., Circulation 75, No. 2, pp. 369–378, 1987.

Entrainment of Ventricular Tachycardia: Explanation for Surface Electrocardiographic Phenonmena by Analysis of Electrograms Recorded Within the Tachycardia Circuit, Almendral et al. Circulation 77, No. 3 pp. 569–580, 1988.

Radio Frequency Catheter Ablation of Ventricular Tachycardia in Patient with Coronary Artery Disease, Morady et al., Circulation vol. 87, No. 2, Feb. 1993, pp. 363–372.

Adaptive Noise Cancelling: Principles and Applications, Widrow et al, Proceedings of the IEEE, Dec. 1975, pp. 1692, 1710.

A Morphological Method for Separation of Ventricular Tachycardia from Ventricular Fibrillation on Intracardiac Electrograms, Jenkins et al., Annual Internatonal Conference of the IEEE Engineering in Medicine and Biology Society, vol. 13, No. 2, 1991, pp. 0742.

Correlation Template Analysis of Intracardiac Electrograms, Murphy et al., Annual International Conference of the IEEE Engineering in Medicine Biology Society, vol. 13, No. 2, 1991, pp. 0736–0737.

A Cyclostationary Least Mean Squares Algorithm for Discrimination of Ventricular Tachycardia from Sinus Rhythm, Finelli et al., Ann. Int. Conf. of the IEEE Eng. in Medicine and Biology Society, vol. 13, No. 2, 1991, pp. 0740–0741.

Regional Control of Atrial Fibrillation by Rapid Pacing in Conscious Dogs, Allessie et al., Circulation, vol. 84, No. 4, pp. 1689–1697.

R.D. Throne, et al., "Use of Tachycardia Templates for Recognition of Recurrent Monomorphic Ventricular Tachycardia," *Proceedings Computers in Cardiology,* Sep. 1989, pp. 171–174, XP000147052, IEEE Computer Society Press, Los Alamitos, California, U.S.

DiLorenzo, et al., "Computer Modeling: Using Computers to Assist in the Localization of Ventricular Tachycardia," *Proceedings Computers in Cardiology,* Sep. 1997, pp. 213–216, XP00030909373, IEEE Computer Society Press, The Institute of Electrical and Electronics Engineers, Inc., Los Alamitos, California, U.S.

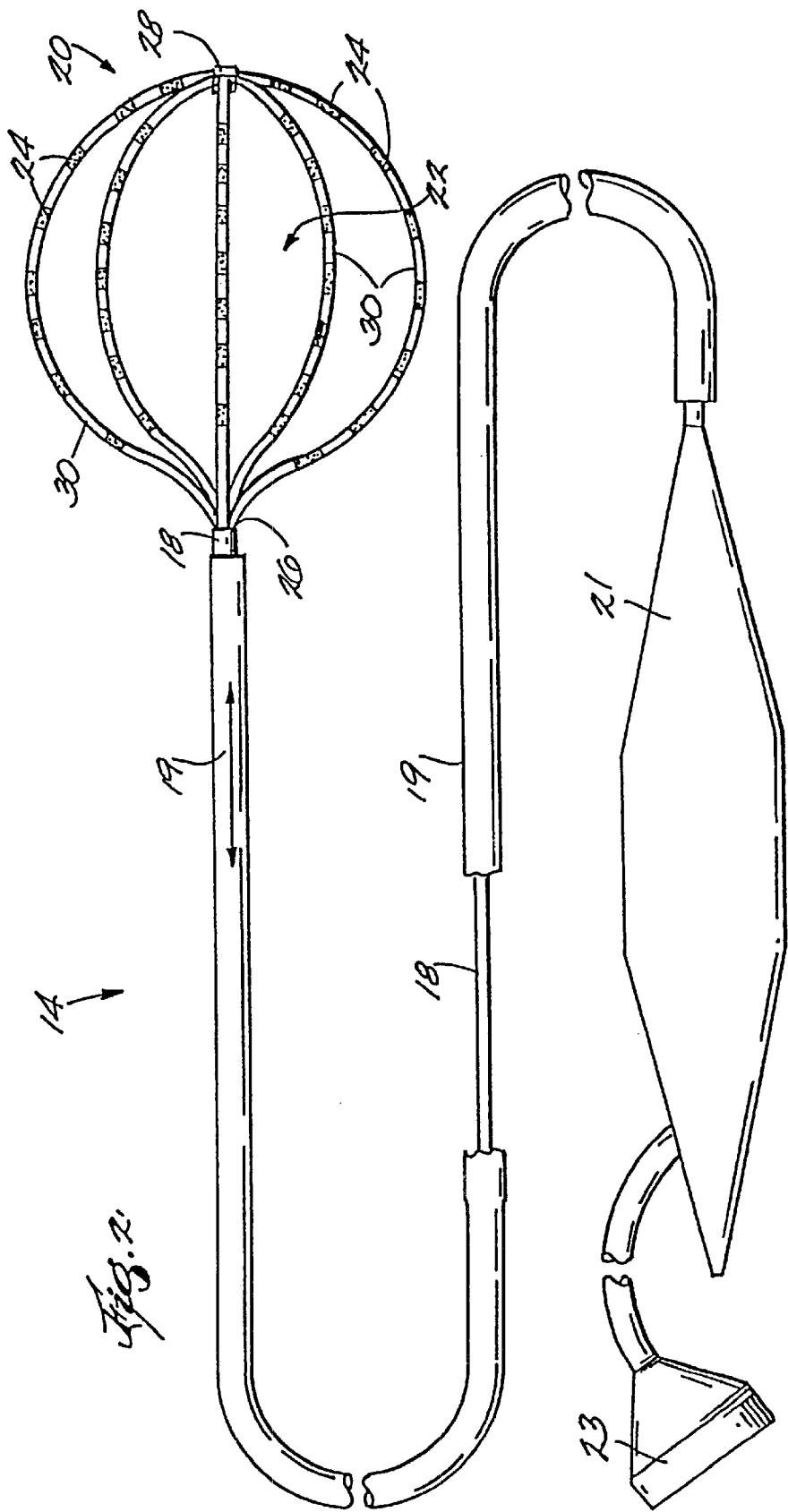

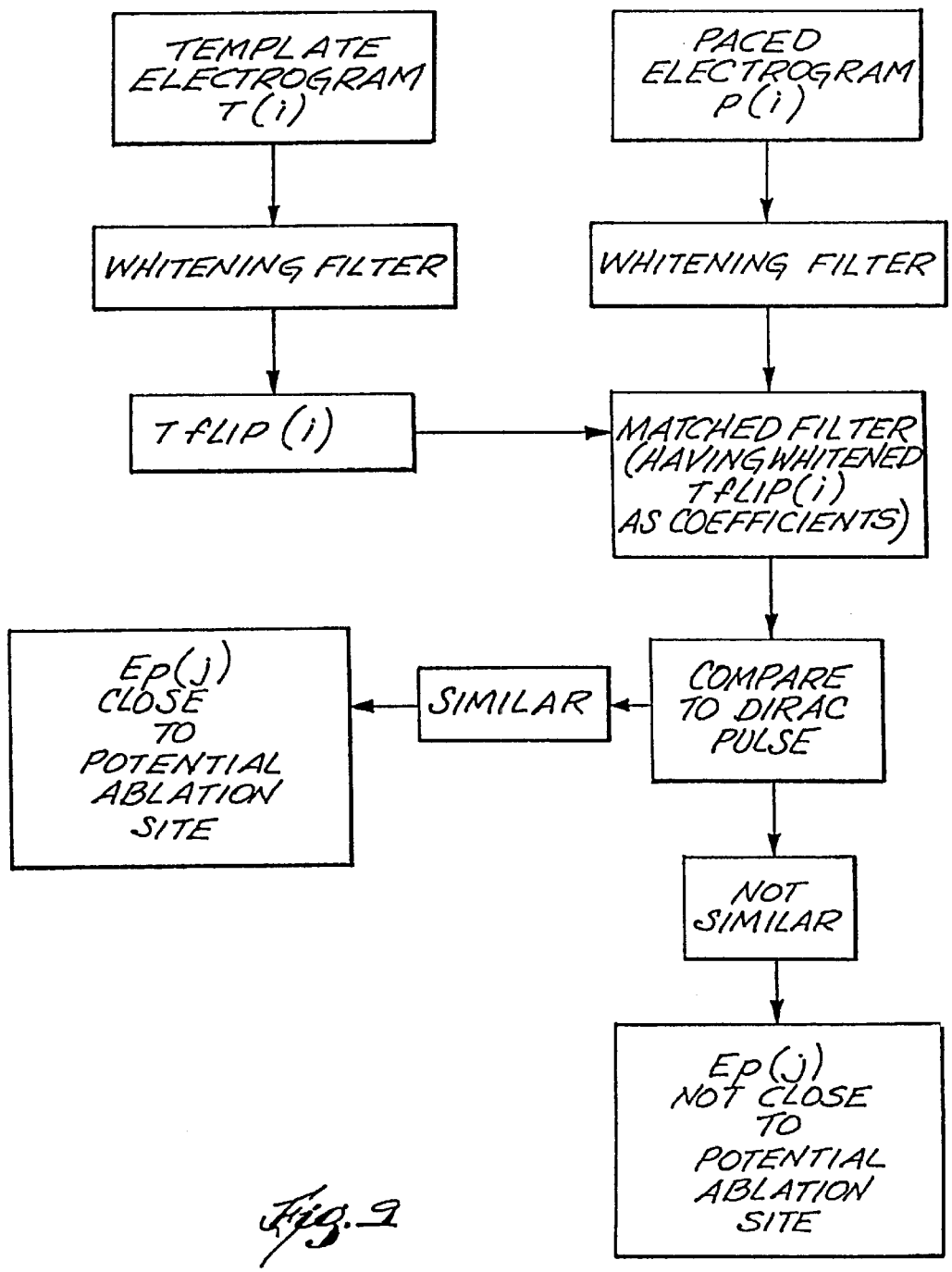

| | FILTER OUTPUT (P3/5) |
|---|---|
| 4 2 7 5 1 10 3 8 9 6 | |

| | | |
|---|---|---|
| 4 2 7 5 1 \| 10 3 8 9 6 | 4 2 4 | 1 2 4 5 7 |
| 4 \| 2 7 5 1 10 \| 3 8 9 6 | 5 | 1 2 5 7 10 |
| 4 2 \| 7 5 1 10 3 \| 8 9 6 | 5 | 1 3 5 7 10 |
| 4 2 7 \| 5 1 10 3 8 \| 9 6 | 5 | 1 3 5 8 10 |
| 4 2 7 5 \| 1 10 3 8 9 \| 6 | 8 | 1 3 8 9 10 |
| 4 2 7 5 1 \| 10 3 8 9 6 \| | 8 | 3 6 8 9 10 |
| | 9 | |
| | 6 | |

Fig. 14B

```
┌─────────────────────┐      ┌──────────────┐
│ 4 2 7 5 1 10 3 8 9 6│      │FILTER OUTPUT │
└─────────────────────┘      │   P(4/5)     │
                             └──────────────┘
                                   4
                                   2
                                   7
   ┌──────────┬──────────┐         5      ┌─────────┐
   │ 4 2 7 5 1│ 10 3 8 9 6│                │ 1 2 4 5 7│
   └──────────┴──────────┘                └─────────┘

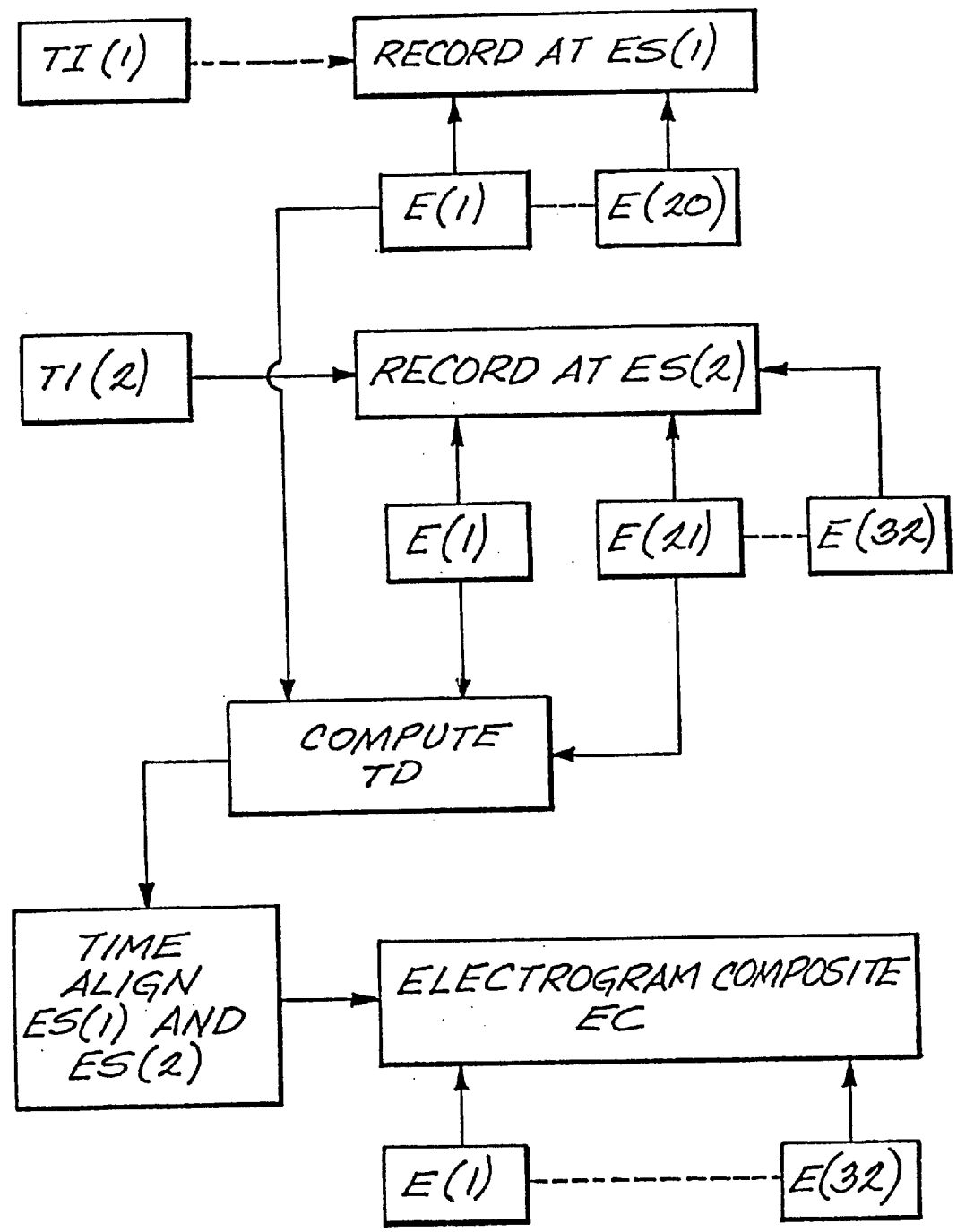
Fig. 2.1

SYSTEMS AND METHODS FOR ACQUIRING AND ANALYZING ELECTROGRAMS IN MYOCARDIAL TISSUE

This is a Continuation of application Ser. No. 09/247,442 filed on Feb. 10, 1999, which is a continuation of 08/955,328 filed Oct. 21, 1997, now U.S. Pat. No. 5,954,662, which is a divisional of application Ser. No. 08/393,158, filed Feb. 17, 1995, now U.S. Pat. No. 5,711,305.

FIELD OF THE INVENTION

The invention relates to systems and methods for acquiring, measuring, and analyzing electrocardiograms.

BACKGROUND OF THE INVENTION

Normal sinus rhythm of the heart begins with the sinoatrial node (or "SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is. next delivered via the atrioventricular node (or "AV node") and the bundle of HIS (or "HIS bundle") to myocardial tissue cells of the ventricles. The depolarization. of these cells propagates across the ventricles, causing the ventricles to contract.

This conduction system results in the described, organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called "conduction blocks") can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates errant, circular propagation patterns, called "circus motion." The circus motion also disrupts the normal depolarization patterns, thereby disrupting the normal contraction of heart tissue.

The aberrant conductive pathways create abnormal, irregular, and sometimes life-threatening heart rhythms, called arrhythmias. An arrhythmia can take place in the atria, for example, as in atrial tachycardia (AT) or atrial flutter (AF). The arrhythmia can also take place in the ventricle, for example, as in ventricular tachycardia (VT).

In treating arrhythmias, it is essential that the location of the sources of the aberrant pathways (call foci) be located. Once located, the tissue in the foci can be destroyed, or ablated, by heat, chemicals, or other means. Ablation can remove the aberrant conductive pathway, restoring normal myocardial contraction.

Today, physicians examine the propagation of electrical impulses in heart tissue to locate aberrant conductive pathways. The techniques used to analyze these pathways, commonly called "mapping," identify regions in the heart tissue, called foci, which can be ablated to treat the arrhythmia.

One form of conventional cardiac tissue mapping techniques uses multiple electrodes positioned in contact with epicardial heart tissue to obtain multiple electrograms. The physician stimulates myocardial tissue by introducing pacing signals and visually observes the morphologies of the electrograms recorded during pacing, which this Specification will refer to as "paced electrograms." The physician visually compares the patterns of paced electrograms to those previously recorded during an arrhythmia episode to locate tissue regions appropriate for ablation. These conventional mapping techniques require invasive open heart surgical techniques to position the electrodes on the epicardial surface of the heart.

Conventional epicardial electrogram processing techniques used for detecting local electrical events in heart tissue are often unable to interpret electrograms with multiple morphologies. Such electrograms are encountered, for example, when mapping a heart undergoing ventricular tachycardia (VT). For this and other reasons, consistently high correct foci identification rates (CIR) cannot be achieved with current multi-electrode mapping technologies.

Another form of conventional cardiac tissue mapping technique, called pace mapping, uses a roving electrode in a heart chamber for pacing the heart at various endocardial locations. In searching for the VT foci, the physician must visually compare all paced electrocardiograms (recorded by twelve lead body surface electrocardiograms (ECG's)) to those previously recorded during an induced VT. The physician must constantly relocate the roving electrode to a new location to systematically map the endocardium.

These techniques are complicated and time consuming. They require repeated manipulation and movement of the pacing electrodes. At the same time, they require the physician to visually assimilate and interpret the electrocardiograms.

Furthermore, artifacts caused by the pacing signals can distort the electrocardiograms. The pacing artifacts can mask the beginning of the Q-wave in the electrocardiogram. In body surface mapping, the morphology of the pacing artifact visually differs from the morphology of the electrocardiogram. A trained physician is therefore able to visually differentiate between a pacing artifact and the electrocardiogram morphology. This is not always the case in endocardial or epicardial mapping, in which there can be a very close similarity between the morphology of the pacing artifact and the bipolar electrogram morphology. Under the best conditions, the pacing artifact and electrogram complex are separated in time, and therefore can be distinguished from one another by a trained physician. Under other conditions, however, the presence of the pacing artifact can sometimes mask the entire bipolar electrogram. In addition, its likeness to the bipolar electrogram often makes it difficult or impossible for even a trained physician to detect the beginning of depolarization with accuracy.

There thus remains a real need for cardiac mapping and ablation systems and procedures that simplify the analysis of electrograms and the use of electrograms to locate appropriate arrhythmogenic foci.

SUMMARY OF THE INVENTION

In accordance with one aspect of the invention, a system is provided for acquiring and analyzing electrograms in myocardial tissue. In one embodiment, the system includes a member supporting multiple electrodes in a three dimensional, radially expanded array adapted to be in operative association with a region of heart tissue; a first processing element including a pacing module and a signal processing module coupled to the multiple electrodes to acquire a sample of a cardiac event by placing the heart at a predetermined location while conditioning the multiple electrodes to sense paced electrograms occurring in the tissue region during pacing; and a second processing element including means for electronically comparing the sample to a template of a cardiac event of known diagnosis and generating an output based upon the comparison, whereby the output provides a diagnostic indicator based upon pacing.

In accordance with a further aspect of the invention, a method is provided for acquiring and analyzing electrograms in myocardial tissue. In one embodiment, the method includes the steps of deploying a three dimensional, radially expanded array of multiple electrodes in operative association with a region of heart tissue; acquiring a sample of a cardiac event by placing the heart at a predetermined location using the multiple electrodes, while conditioning the multiple electrodes to sense paced electrograms occurring in the tissue region during pacing, and electronically comparing the sample to a template of a cardiac event of known diagnosis and generating an output based upon the comparison, whereby the output provides a diagnostic indicator based upon pacing.

Other features and advantages of the inventions are set forth in the following Description and Drawings, as well as in the appended Claims.

BRIEF DESCRIPTION OF THE DRAWINGS

FIGS. 7A and 7B are, respectively, a flow chart and illustrative wave shape showing a symmetry matching technique that the process controller shown in FIG. 4A can employ for matching electrograms according to the invention;

FIG. 9 is a flow chart showing a matched filtering technique that the process controller shown in FIG. 4A can employ for matching electrograms according to the invention;

FIG. 14B is a diagram showing the implementation of the filtering technique shown in FIG. 14A as a median filter;

FIG. 14C is a diagram showing the implementation of the filtering technique shown in FIG. 14A as a non-median filter;

FIG. 21 is a diagrammatic flow chart showing the operation of the time-sequential mode of the process controller shown in FIG. 1 in creating an. electrogram composite over different time intervals;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

Description of the Preferred Embodiments

Figure 1A:
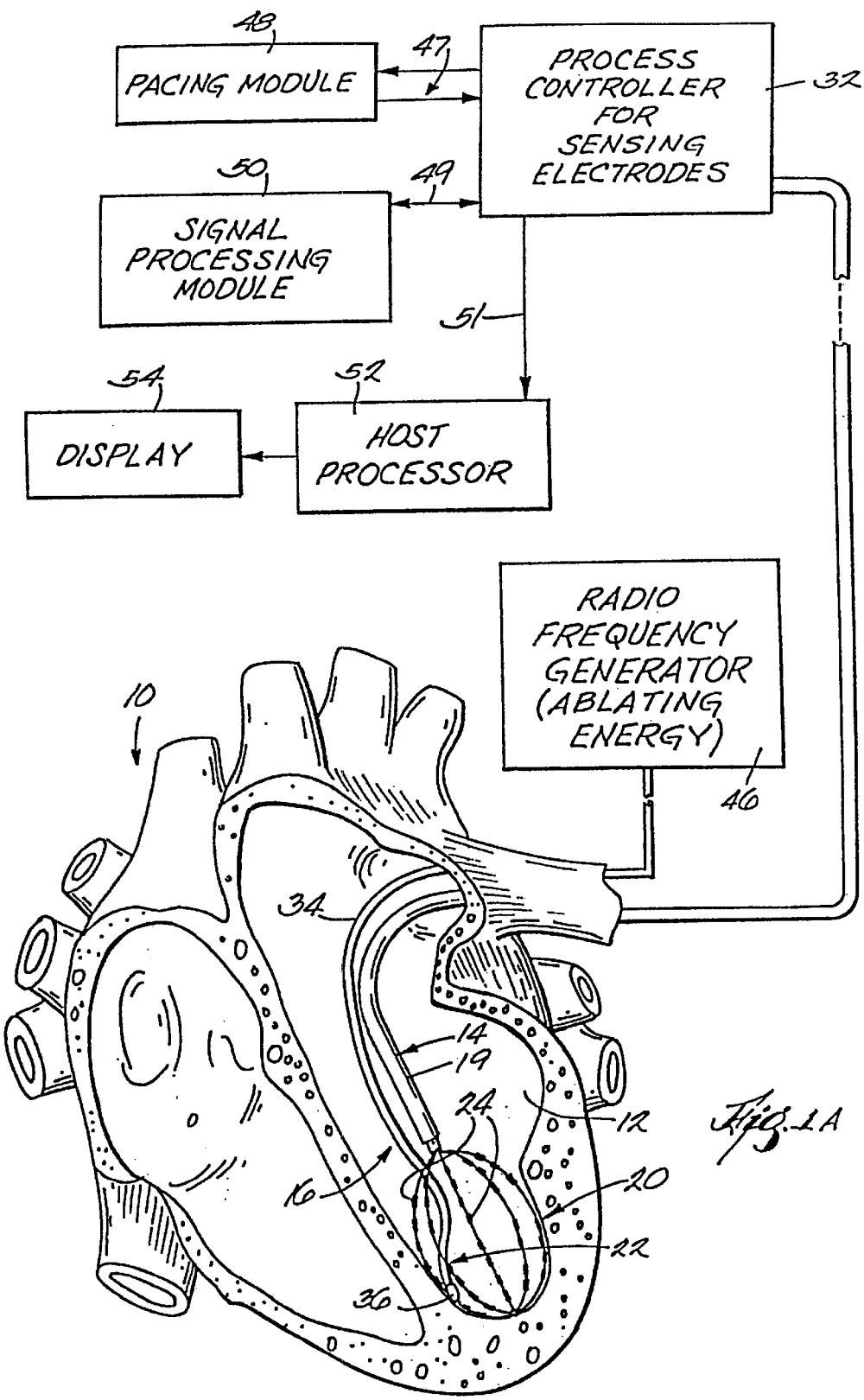
FIG. 1A is a diagrammatic view of a system, which embodies the features of the invention, for accessing a targeted tissue region in the body for diagnostic or therapeutic purposes.

FIG. 1A shows the components of a system 10 for analyzing body tissue biopotential morphologies for diagnostic or therapeutic purposes. The illustrated embodiment shows the system 10 being used to examine the depolarization of heart tissue that is subject to an arrhythmia. In this embodiment, the system 10 serves to locate an arrhythmogenic focus for removal by ablation. The invention is well suited for use in conducting electrical therapy of the heart.

Still, it should be appreciated that the invention is applicable for use in other regions of the body where tissue biopotential morphologies can be ascertained by analyzing electrical events in the tissue. For example, the various aspects of the invention have application in procedures for analyzing brain or neurologic tissue.

FIG. 1A shows the system 10 analyzing endocardial electrical events, using catheter-based, vascular access techniques. Still, many aspects of the invention can be used in association with techniques that do not require any intrusion into the body, like surface electrocardiograms or electroencephalograms. Many of the aspects of the invention also can be used with invasive surgical techniques, like in open chest or open heart surgery, or during brain surgery.

Figure 1B:
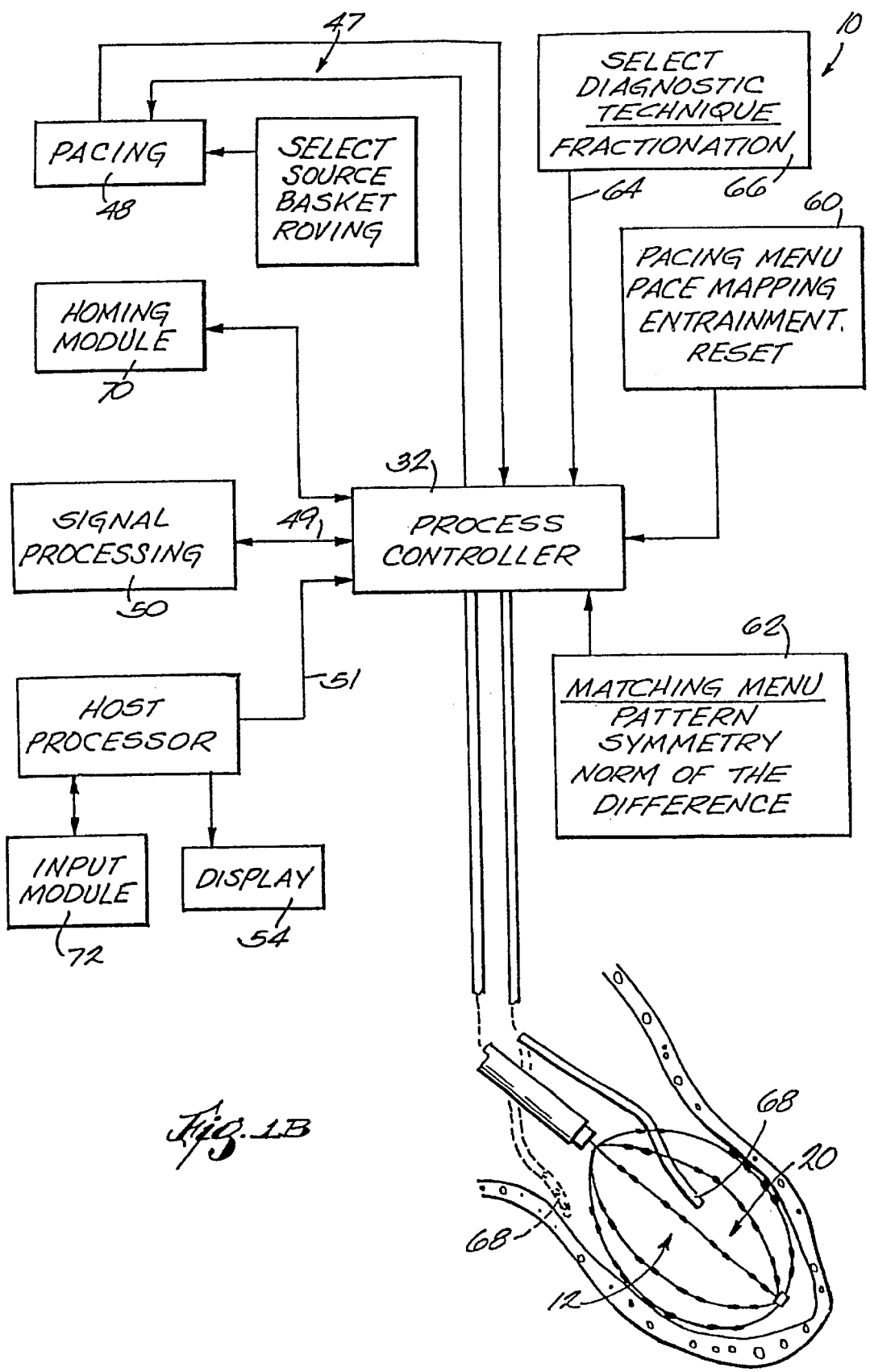
FIG. 1B is a diagrammatic view of the system shown in FIG. 1A, with the inclusion of a roving pacing probe and additional features to aid the physician in conducting diagnosis and therapeutic techniques according. to the invention.

In particular, FIG. 1A shows the system 10 analyzing electrical events within a selected region 12 inside a human heart. FIGS. 1A and 1B generally show the system 10 deployed in the left ventricle of the heart. Of course, the system 10 can be deployed in other regions of the heart, too. It should also be noted that the heart shown in the FIG. 1 is not anatomically accurate. FIGS. 1A and 1B show the heart in diagrammatic form to demonstrate the features of the invention.

The system 10 includes a mapping probe 14 and an ablation probe 16. In FIG. 1A, each is separately introduced into the selected heart region 12 through a vein or artery (typically the femoral vein or artery) through suitable percutaneous access.

Alternatively, the mapping probe 14 and ablation probe 16 can be assembled-in an integrated structure for simultaneous introduction and deployment in the heart region 12.

Further details of the deployment and structures of the probes 14 and 16 are set forth in pending U.S. patent application Ser. No. 08/033,641, filed Mar. 16, 1993, entitled "Systems and Methods Using Guide Sheaths for Introducing, Deploying, and Stabilizing Cardiac Mapping and Ablation Probes."

The mapping probe 14 has a flexible catheter body 18. The distal end of the catheter body 18 carries a three dimensional multiple-electrode structure 20. In the illustrated embodiment, the structure 20 takes the form of a basket defining an open interior space 22 (see FIG. 2). It should be appreciated that other three dimensional structures could be used.

Figure 2B:
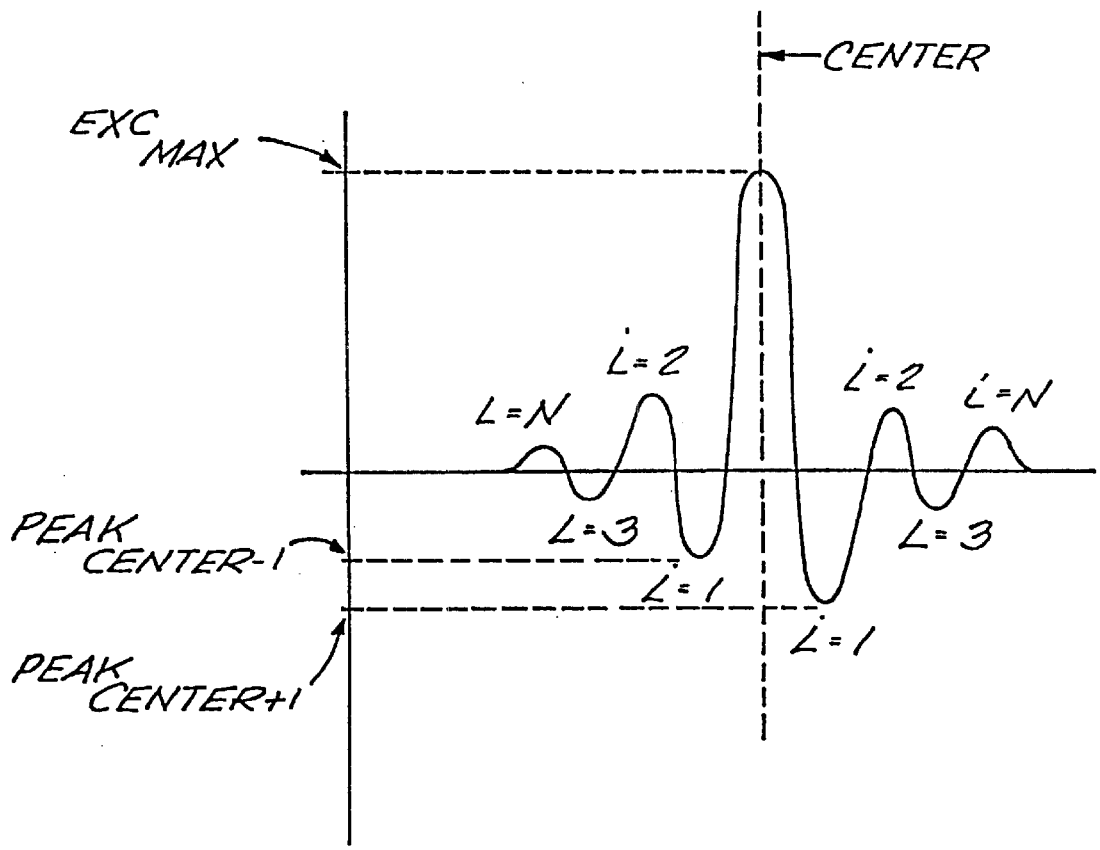
FIG. 2 is an enlarged perspective view of a multiple-electrode structure used in association with the system shown in FIG. 1.

As FIG. 2 shows, the illustrated basket structure 20 comprises a base member 26 and an end cap 28. Generally flexible splines 30 extend in a circumferentially spaced relationship between the base member 26 and the end cap 28.

The splines 30 are preferably made of a resilient, biologically inert material, like Nitinol metal or silicone rubber. The splines 30 are connected between the base member 26 and the end cap 28 in a resilient, pretensed, radially expanded condition, to bend and conform to the endocardial tissue surface they contact. In the illustrated embodiment (see FIG. 2), eight splines 30 form the basket structure 20. Additional or fewer splines 30 could be used.

The splines 30 carry an array of electrodes 24. In the illustrated embodiment, each spline 30 carries eight electrodes 24. Of course, additional or fewer electrodes 24 can be used.

A slidable sheath 19 is movable along the axis of the catheter body 18 (shown by arrows in FIG. 2). Moving the sheath 19 forward causes it to move over the basket structure 20, collapsing it into a compact, low profile condition for introducing into the heart region 12. Moving the sheath 19 rearward frees the basket structure 20, allowing it to spring open and assume the pretensed, radially expanded position shown in FIG. 2. The electrodes are urged into contact against the surrounding heart tissue.

Further details of the basket structure are disclosed in pending U.S. patent application Ser. No. 08/206,414, filed Mar. 4, 1994, entitled "Multiple Electrode Support Structures."

In use, the electrodes 24 sense electrical events in myocardial tissue for the creation of electrograms. The electrodes 24 are electrically coupled to a process controller 32 (see FIG. 1A). A signal wire (not shown) is electrically coupled to each electrode 24. The wires extend through the body 18 of the probe 14 into a handle 21, in which they are coupled to an external multiple pin connector 23. The connector 23 electrically couples the electrodes to the process controller 32.

Alternatively, multiple electrode structures can be located epicardially using a set of catheters individually. introduced through the coronary vasculature (e.g., retrograde through the aorta or coronary sinus), as disclosed in PCT/US94/01055 entitled "Multiple Intravascular Sensing Devices for Electrical Activity."

Figure 3:
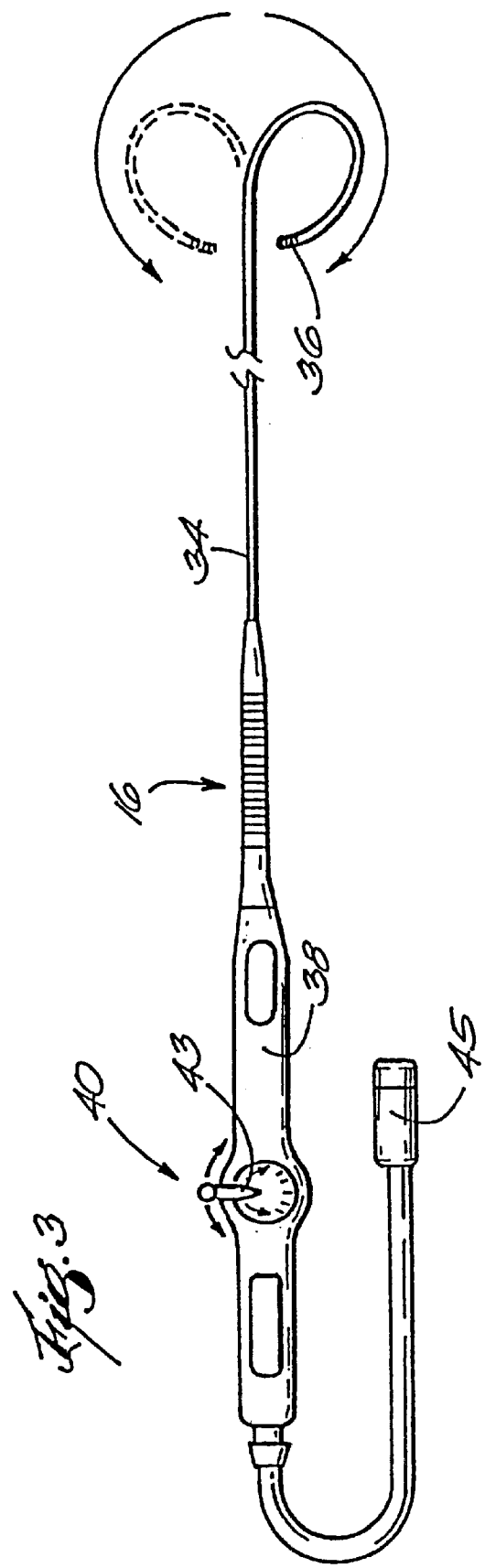
FIG. 3 is an enlarged view of an ablation probe usable in association with the system shown in FIGS. 1A and 1B.

The ablation probe 16 (see FIG. 3) includes a flexible catheter body 34 that carries one or more ablation electrodes 36. For the sake of illustration, FIG. 3 shows a single ablation electrode 36 carried at the distal tip of the catheter body 34. Of course, other configurations employing multiple ablation electrodes are possible, as described in pending U.S. patent application Ser. No. 08/287,310, filed Aug. 8, 1994, entitled "Systems and Methods for Ablating Heart Tissue Using Multiple Electrode Elements."

A handle 38 is attached to the proximal end of the catheter body 34. The handle 38 and catheter body 34 carry a steering mechanism 40 for selectively bending or flexing the catheter body 34 along its length, as the arrows. in FIG. 3 show.

The steering mechanism 40 can vary. For example, the steering mechanism can be as shown in U.S. Pat. No. 5,254,088, which is incorporated herein by reference.

A wire (not shown) electrically connected to the ablation electrode 36 extends through the catheter body 34 into the handle 38, where it is electrically coupled to an external connector 45. The connector 45 connects the electrode 36 to a generator 46 of ablation energy. The type of energy used for ablation can vary. Typically, the generator 46 supplies electromagnetic radio frequency energy, which the electrode 36 emits into tissue. A radio frequency generator Model EPT-1000, available from EP Technologies, Inc., Sunnyvale, Calif. can be used for this purpose.

In use, the physician places the ablation electrode 36 in contact with heart tissue at the site identified for ablation.

The ablation electrode emits ablating energy to heat and thermally destroy the contacted tissue.

According to the features of the invention, the process controller 32 employs electrogram matching to automatically locate for the physician the site or sites potentially appropriate for ablation.

I. Electrogram Matching

The process controller 32 is operable to sense electrical events in heart tissue and to process and analyze these events to achieve the objectives of the invention. The process controller 32 is also selectively operable to induce electrical events by transmitting pacing signals into heart tissue. More particularly, the process controller 32 is electrically coupled by a bus 47 to a pacing module 48, which paces the heart sequentially through individual or pairs of electrodes to induce depolarization. Details of the process controller 32 and pacing module 48 are described in copending U.S. patent application Ser. No. 08/188,316, filed Jan. 28, 1994, and entitled "Systems and Methods for Deriving Electrical Characteristics of Cardiac Tissue for Output in Iso-Characteristic Displays."

The process controller 32 is also electrically coupled by a bus 49 to a signal processing module 50. The processing module 50 processes cardiac signals into electrograms. A Model TMS 320C31 processor available from Spectrum Signal Processing, Inc. can be used for this purpose.

The process controller 32 is further electrically coupled by a bus 51 to a host processor 52, which processes the input from the electrogram processing module 50 in accordance with the invention to locate arrhythmogenic foci. The host processor 32 can comprise a 486-type microprocessor.

According to the invention, the process controller 32 operates in two functional modes, called the sampling mode and the matching mode.

In the sampling mode, the physician deploys the basket structure 20 in the desired heart region 12. To assure adequate contact is made in the desired region 12, the physician may have to collapse the basket structure 20, rotate it, and then free the basket structure 20. The degree of contact can be sensed by the process controller 32 in various ways. For example, the process controller 32 can condition the pacing module 48 to emit pacing signals through a selected electrode 24 or pair of electrodes 24. The process controller 32 conditions the electrodes 24 and processing module 50 to detect electrograms sensed by a desired number of the electrodes 24. The processing module can also ascertain the desired degree of contact by measuring tissue impedance, as described in copending patent application Ser. No. 08/221,347, filed Mar. 31, 1994, and entitled "Systems and Methods for Positioning. Multiple Electrode Structures in Electrical Contact with the Myocardium."

Once the basket structure 20 is properly positioned, the process controller 32 conditions the electrodes 24 and signal processing module 50 to record electrograms during a selected cardiac event having a known diagnosis. In the sampling mode, the process controller 32 typically must condition the pacing module 48 to pace the heart until the desired cardiac event is induced. Of course, if the patient spontaneously experiences the cardiac event while the structure 20 is positioned, then paced-induction is not required.

The processor controller 32 saves these electrograms in the host processor 52. The process controller 32 creates templates of selected electrogram morphologies by any conventional method, e.g., by having the physician manually select representative electrogram morphologies. At the end of the sampling mode, the process controller 32 typically must condition the pacing module 48 to pace terminate the cardiac event, or the physician may apply a shock to restore normal sinus rhythm.

The matching mode is conducted without altering the position of the multiple electrode structure 20 in the heart region 12, so that the electrodes 24 occupy the same position during the matching mode as they did during the sampling mode.

In the matching mode, the process controller 32 conditions the pacing module 48 to pace the heart in a prescribed manner without inducing the cardiac event of interest, while conditioning the signal processing module 50 to record the resulting electrograms. The process controller 32 operates the host processor 52 to compare the resulting paced electrogram morphologies to the electrogram morphology templates collected-during the sampling mode. Based upon this comparison, the host processor 52 generates an output that identifies the location of the electrode or electrodes 24 on the structure 20 that are close to a potential ablation site.

A. The Sampling Mode

As before generally described, the process controller 32 operates in the sampling mode while the heart is experiencing a selected cardiac event of known diagnosis and the basket structure 20 is retained in a fixed location in the region 12. In the illustrated and preferred embodiment, the selected event comprises an arrhythmia that the physician seeks to treat, for example, ventricular tachycardia (VT), or atrial tachycardia (AT), or atrial fibrillation (AF).

Figure 4A:
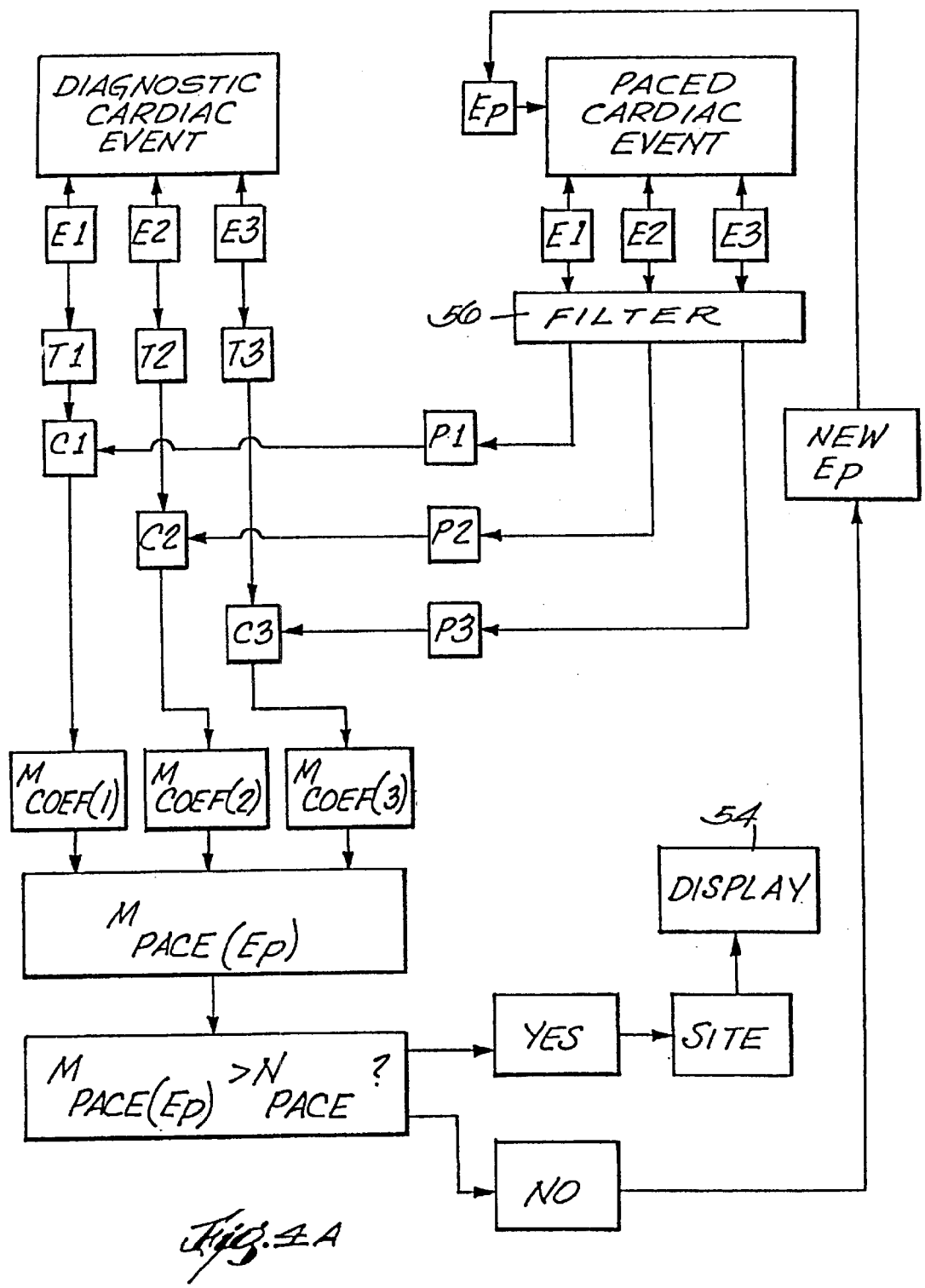
FIG. 4A is a diagrammatic view of the process controller shown in FIGS. 1A and 1B, which locates by electrogram matching a site appropriate for ablation.

As FIG. 4A shows, during the sampling mode, the signal processing module 50 processes the electrogram morphologies obtained from each electrode during the known cardiac event (designated for the purpose of illustration as E1 to E3 in FIG. 4A). The electrograms may be recorded unipolar (between an electrode 24 and a reference electrode, not shown) or bipolar (between electrodes 24 on the structure The host processor 52 creates a digital, event-specific template for the morphology sensed at each electrode (designated for the purpose of illustration as T1 to T3 in FIG. 4A). The event-specific templates T1 to T3 for each electrode E1 to E3 can be based upon electrogram morphology from one heart beat or a specified number of heart beats. The event-specific template T1 to T3 for each electrode E1 to E3 can be created by, for example, having the physician manually select representative electrogram morphologies.

If the arrhythmia event is not polymorphic, the template preferably comprises one heart beat and is updated beat by beat. Also preferably, though not essential, the starting point of the template should coincide with the beginning of the depolarization and extend one beat from that point. However, if the arrhythmia event under study is polymorphic, it may be necessary to extend the template over several beats. For example, in bigeminy cases, the template should preferably extend over two beats.

The host processor 52 retains the set of event-specific templates T1 to T3 in memory. The processor 52 can, for an individual patient, retain sets of event-specific templates for different cardiac events. For example, a patient may undergo different VT episodes, each with a different morphology. The processor 52 can store templates for each VT episode for analysis according to the invention. The templates can be downloaded to external disk memory for off-line matching at a subsequent time, as will be described later. Templates can also be generated based upon mathematical modeling or empirical data and stored for later matching for diagnostic purposes.

B. The Matching Mode

In the matching mode, the process controller 32 operates the pacing module 48 to apply pacing signals sequentially to each of the individual electrodes. The pacing electrode is designated Ep in FIG. 4A.

The pacing signal induces depolarization, emanating at the location of the pacing electrode Ep. The process controller 32 operates the signal processing module 50 to process the resulting paced electrogram morphologies sensed at each electrode (again designated E1 to E3 for the purpose of illustration in FIG. 4A) during pacing by the selected individual electrode Ep. The processed paced electrograms are designated P1 to P3 in FIG. 4A.

The paced morphology P1 to P3 at each electrode can be from one heart beat or a specified number of heart beats, provided that the length of the morphologies P1 to P3 is not shorter than the length of the event-specific templates T1 to T3 for the same electrodes E1 to E3 obtained during the sampling mode.

Different conventional pacing techniques can be used to obtain the paced morphologies P1 to P3. For example, conventional pace mapping can be used, during which the pace rate is near the arrhythmia rate, but arrhythmia is not induced.

For reasons that will be explained later, conventional entrainment or reset pacing is the preferred technique. During entrainment pacing, the pacing rate is slightly higher than and the period slightly lower than that observed during the arrhythmia event, thereby increasing the rate of the induced arrhythmia event. Further details of entrainment pacing are found in Almendral et al., "Entrainment of Ventricular Tachycardia: Explanation for Surface Electrocardiographic Phenomena by Analysis of Electrograms Recorded Within the Tachycardia Circuit," *Circulation*, vol. 77, No. Mar. 3, 1988, pages 569 to 580, which is incorporated herein by reference.

Regardless of the particular pacing technique used, the pacing stimulus may be monophasic, biphasic, or triphasic.

In the matching mode, while pacing at an individual one of the electrodes Ep, the host processor 52 compares the paced morphology P1 to P3 obtained at each electrode E1 to E3 to the stored event-specific template T1 to T3 for the same electrode E1 to E3. The comparisons (which are designated C1 to C3 in FIG. 4A) can be performed by using matched filtering or correlation functions, as will be described later.

Alternatively, the paced morphologies P1 to P3 can be retained in memory or downloaded to external disk memory for matching at a later time. To accommodate off-line processing, the host processor 52 preferably includes an input module 72 for uploading pregenerated templates and/or paced morphologies recorded at an earlier time. The input module 72 allows templates and paced morphologies to be matched off-line by the host processor 52, without requiring the real time presence of the patient. Alternatively, recorded paced morphologies can be matched in real time using templates generated earlier. The pregenerated templates can represent "typical" biopotential events based upon either real, empirical data, or mathematical models for diagnostic purposes, or reflect earlier biopotential events recorded for the same patient or for a patient having the same or similar prognosis.

For each pacing electrode Ep(j), the host processor 52 generates a matching coefficient $M_{COEF(i)}$ for each electrode E(i) from the comparison C(i) of the pacing morphology P(i) to the template morphology T(i) for the same electrode E(i). Preferably, both j and i=1 to n, where n is the total number of electrodes on the three dimensional structure (which, for the purpose of illustration in FIG. 4A, is 3).

The value of the matching coefficient $M_{COEF(i)}$ is indicative for that electrode E(i) how alike the pacing morphology P(i) is to the event-specific template T(i) for that electrode E(i). The value of $M_{COEF(i)}$ for each electrode E(i) varies as the location of the pacing electrode. Ep(j) changes. Generally speaking, the value of the matching coefficient $M_{COEF(i)}$ for a given electrode E(i) increases in relation to the closeness of the pacing electrode Ep(j) to the arrhythmogenic foci. In the illustrated and preferred embodiment (as FIG. 4A shows), while pacing at an individual one of the electrodes Ep(j), the host processor 52 generates from the matching coefficients $M_{COEF(i)}$ for each electrode E(i) an overall matching factor $M_{PACE(j)}$ for the pacing electrode Ep(j). The value of the overall matching factor $M_{PACE(j)}$ for the pacing electrode Ep(j) is indicative of how alike the overall propagation pattern observed during pacing at the electrode Ep(j) is to the overall propagation pattern recorded on the associated event-specific templates.

The process controller 32 operates the pacing module 48 to apply a pacing signal sequentially to each electrode Ep(j) and processes and compares the resulting electrogram morphologies at each electrode E(i) (including Ep(j)) to the event-specific templates, obtaining the matching coefficients $M_{COEF(i)}$ for each electrode E(i) and an overall matching factor $M_{PACE(j)}$ for the pacing electrode Ep(j), and so on, until every electrode E(i) serves as a pacing electrode Ep(j). $M_{PACE(j)}$ for each pacing electrode can be derived from associated matching coefficients $M_{COEF(i)}$ in various ways.

For example, various conventional averaging techniques can be used. For example, $M_{PACE(j)}$ can be computed as a first order average (arithmetic mean) of $M_{COEF(i)}$ as follows:

$$M_{PACE(j)} = \frac{\sum M_{COEF(i)}}{n}$$

where i=1 to n; or as a weighted arithmetic mean, as follows:

$$M_{PACE(j)} = \sum W(i) M_{COEF(i)}$$

where i=1 to n; $\Sigma W(i)=1$. If $W(i)=1/n$, for each i, then the arithmetic mean is obtained.

Generally speaking, the value of the overall matching factor $M_{PACE(j)}$ increases in relation to the proximity of the particular pacing electrode Ep(j) to a potential ablation site.

Figure 4B:
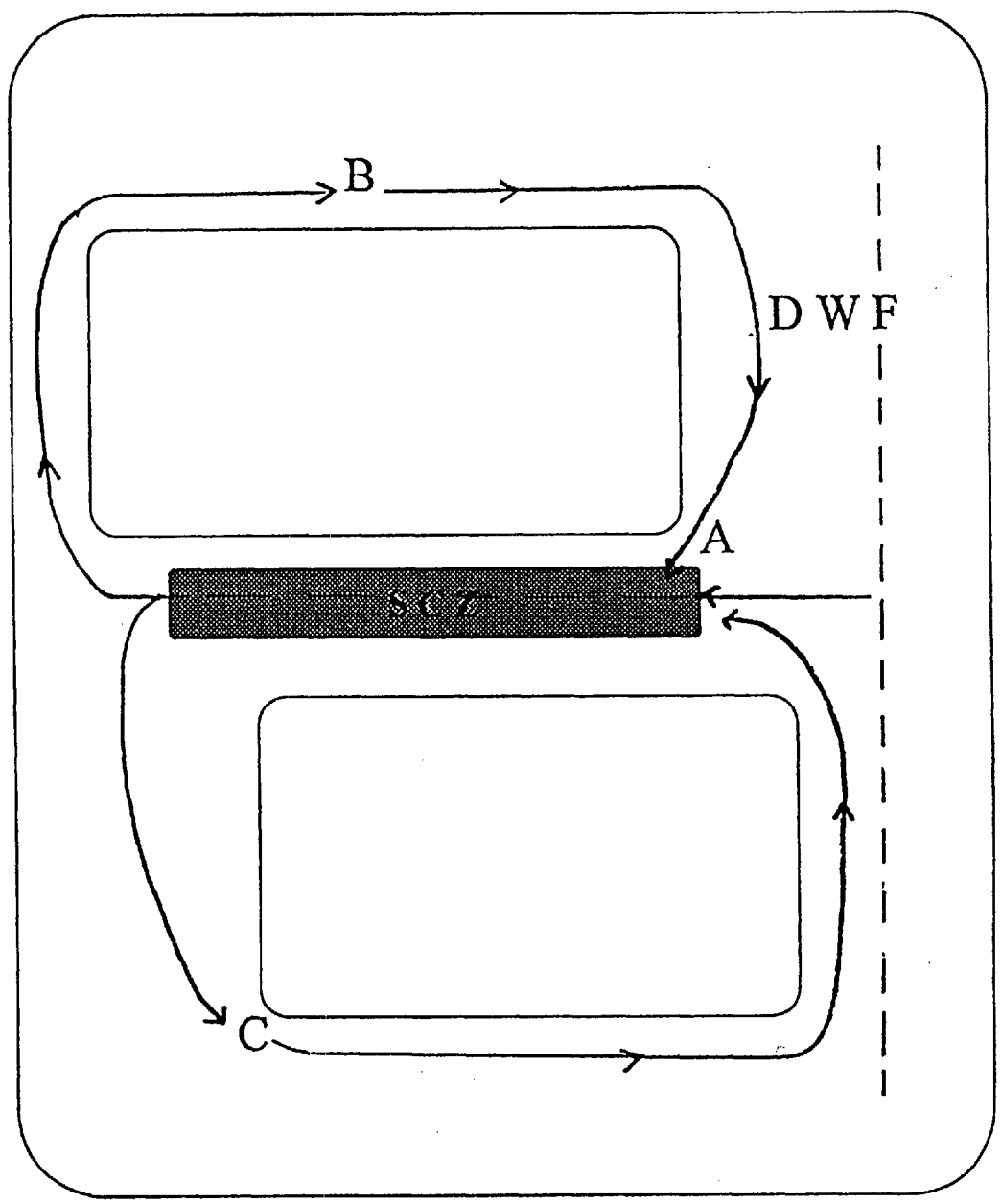
FIG. 4B is a schematic view of a slow conduction zone in myocardial tissue and the circular propagation patterns (called circus motion) it creates.

By way of overall explanation, for VT, the site appropriate for ablation typically constitutes a slow conduction zone, designated SCZ in FIG. 4B. Depolarization wave fronts (designated DWF in FIG. 4B) entering the slow conduction zone SCZ (at site A in FIG. 4B) break into errant, circular propagation patterns (designated B and C in FIG. 4B), called "circus motion." The circus motions disrupt the normal depolarization patterns, thereby disrupting the normal contraction of heart tissue to cause the cardiac event.

The event-specific templates T(i) record these disrupted depolarization patterns. When a pacing signal is applied to a slow conduction zone, the pacing signal gets caught in the same circus motion (i.e., paths B and C in FIG. 4B) that triggers the targeted cardiac event. A large proportion of the associated pacing morphologies P(i) at the sensing electrodes E(i) will therefore match the associated event-specific templates P(i) recorded during the targeted cardiac event. This leads to a greater number of larger matching coefficients $M_{COEF(i)}$ and thus to a larger overall matching factor $M_{PACE(j)}$.

However, when a pacing signal is applied outside a slow conduction zone, the pacing signal does not get caught in the same circus motion. It propagates free of circus motion to induce a significantly different propagation pattern than the one recorded in the templates T(i). A large proportion of the pacing morphologies P(i) at the sensing electrodes E(i) therefore do not match the event-specific templates T(i). This leads to a smaller number of larger matching coefficients $M_{COEF(i)}$ and thus to a smaller overall matching factor $M_{PACE(j)}$.

This is why the overall matching factor $M_{PACE(j)}$ becomes larger the closer the pacing electrode Ep(j) is to the slow conduction zone, which is the potential ablation site. The difference in propagation patterns between pacing inside and outside a slow conduction zone is particularly pronounced during entrainment pacing. For this reason, entrainment pacing is preferred.

Ablating tissue in or close to the slow conduction zone prevents subsequent depolarization. The destroyed tissue is thereby "closed" as a possible path of propagation. Depolarization events bypass the ablated region and no longer become caught in circus motion. In this way, ablation can restore normal-heart function.

The matching of pacing morphologies P(i) to template morphologies T(i) to create the matching coefficient $M_{COEF(i)}$ and the overall matching factor $M_{PACE(i)}$ can be accomplished in various ways. According to the invention, the host processor 52 can employ pattern matching; symmetry matching; matched filtering; cross correlation; or norm of the difference techniques. The following provides an overview of each of these techniques.

1. Pattern Matching

Figure 5:
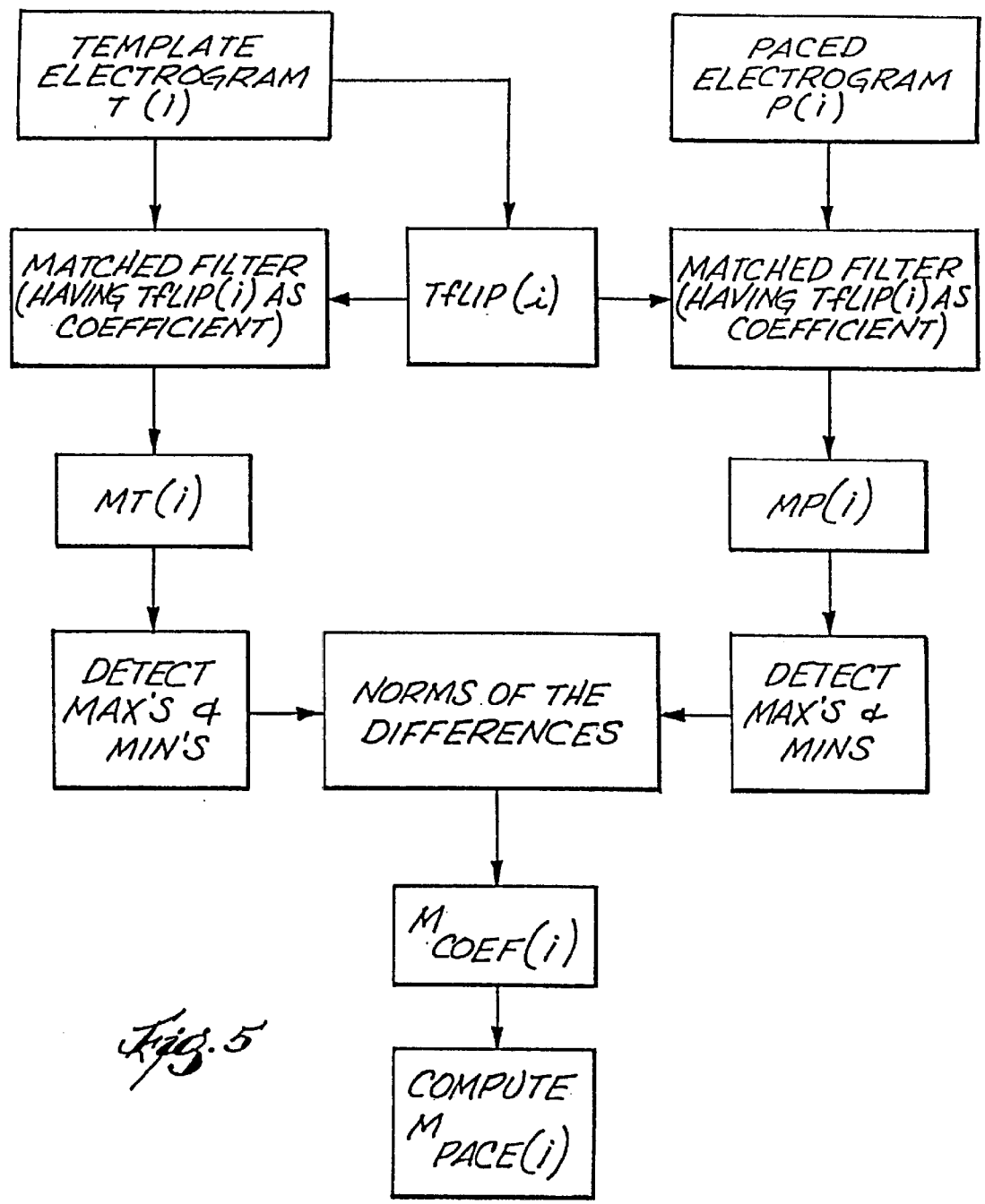
FIG. 5 is a flow chart showing a pattern matching technique that the process controller shown in FIG. 4A can employ for matching electrograms according to the invention.

FIG. 5 diagrammatically shows a pattern matching technique that embodies features of the invention.

Figure 6A:
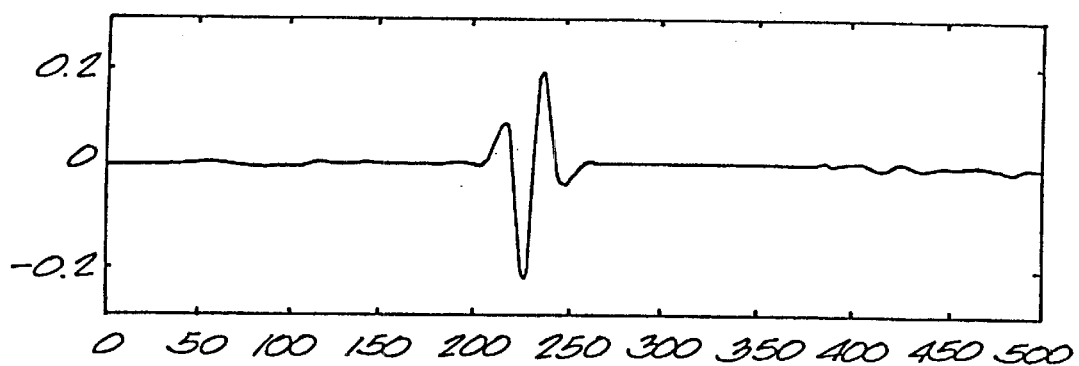
FIGS. 6A to 6E are representative electrogram morphologies processed in accordance with the pattern matching technique shown in FIG. 5.
Figure 6B:
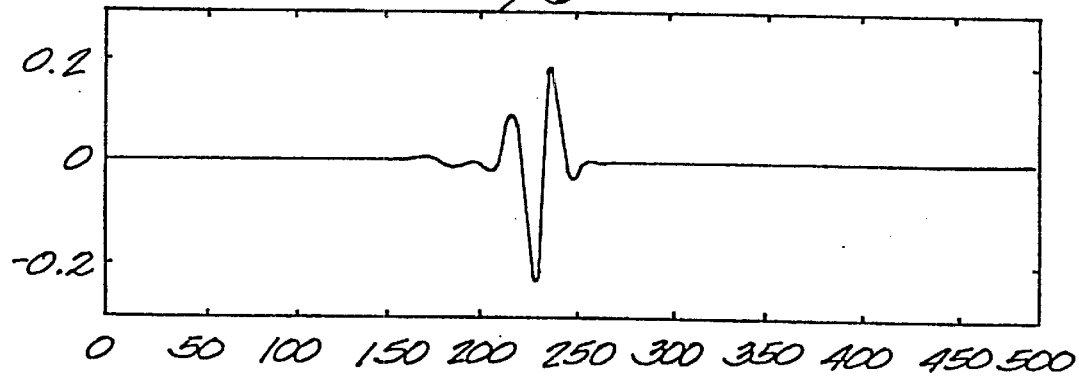
Figure 6C:
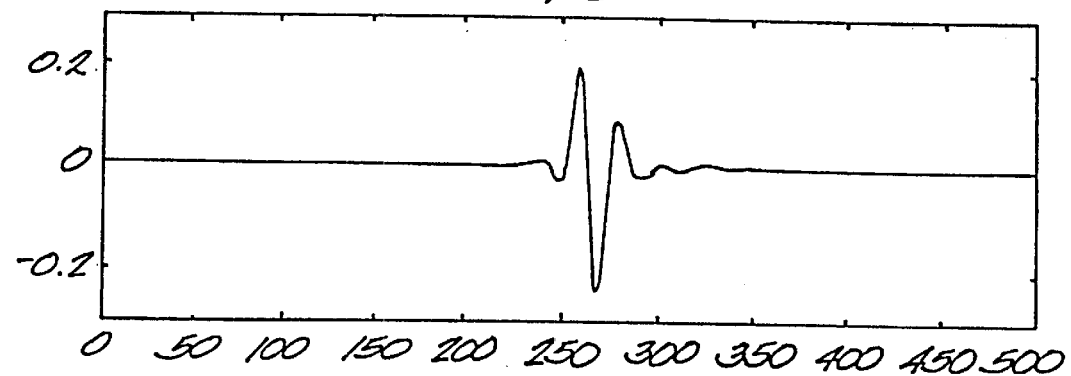
Figure 6D:
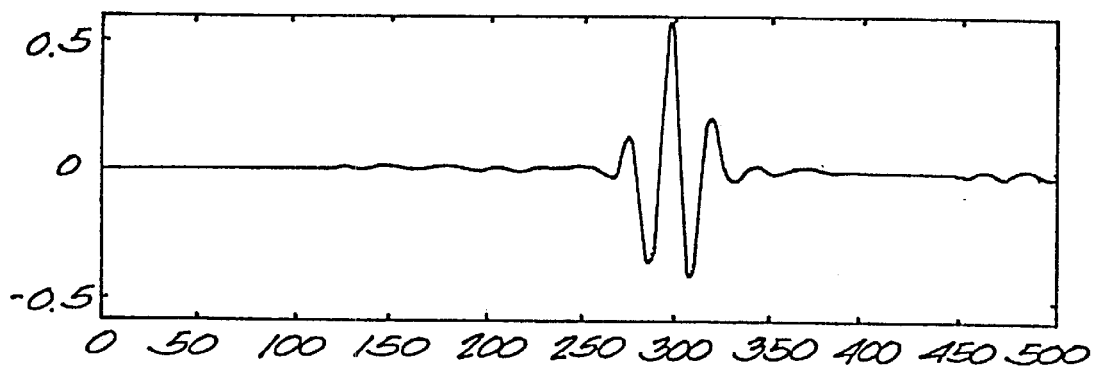
Figure 6E:
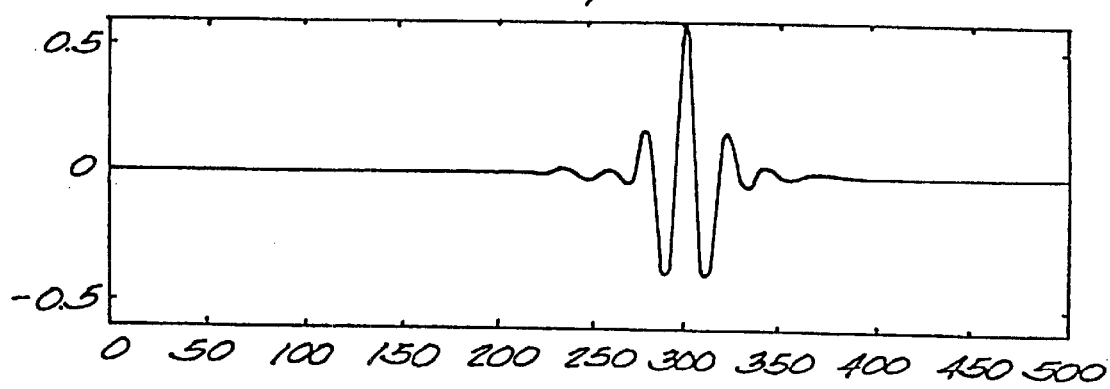

The pattern matching technique matched filters the template T(i) for each electrode E(i) using the same template flipped left to right with respect to time, Tflip(i), as coefficients of the matched filter. FIG. 6B shows a representative template T(i) for a given electrode E(i). FIG. 6C shows Tflip(i), which is the template T(i) (shown in FIG. 6B) flipped right to left. FIG. 6E shows a matched filtered output MT(i), which had T(i) (FIG. 6B) as input and Tflip(i) (FIG. 6C) for the same electrode E(i) as coefficients of the matched filter. As FIG. 6E shows, the matched filtered output MT(i) is, for the electrode E(i), a sequence of alternating maximums and minimums, with their values marking a first pattern employed by this technique.

The pattern matching technique also matched filters the paced electrogram P(i) for each electrode E(i) using an identical matched filter as the one described above. FIG. 6A shows a representative paced electrogram P(i) for the given electrode E(i). FIG. 6D shows the matched filtered output MP(i), using Tflip(i) shown in FIG. 6C as the matched filtered coefficients. Like MT(i), the matched filtered output MP(i) is, for each electrode E(i), a sequence of alternating maximums and minimums, which are used to construct a second pattern.

The pattern matching technique detects the maximums and minimums for the matched filtered template outputs MT(i) and those of MP(i). The pattern matching technique places the maximums and minimums in two odd-length, L-sized model vectors, with the largest excursions at position $$i = \left|\frac{L+1}{2}\right|$$

where L is the total number of local extremes of MT(i) and MP(i). The pattern matching technique computes the norm of the difference between the MP-pattern and the corresponding MT-pattern shifted by an amount, P, that varies from −K to K, where K=L/2. The maximum number of comparisons for n electrodes will be n comparisons for each pacing electrode. Alternatively, one can shift the MP-patterns as just described, keeping the corresponding MT-patterns fixed. The largest excursions are placed in the centers of the template and paced vectors.

For example, assuming
MT(i)={mt(i,1),mt(i,2),mt(i,3)}, and
MP(i)={mp(i,1+p),mp(i,2+p),mp(i,3+p)}, then $$\text{norm}_{(i,p)} = \|MT(i) - MP(i)\| \text{ or}$$

$$\text{norm}_{(i,p)} = \sqrt{\Sigma[mt(i,r) - mp(i,r+p)]^2}$$

where r=1 to 3 and p=−K to K.

The minimum of the above is used as the matching coefficient for the sequence of norms ($M_{COEF(i)}$), i.e.,:

$$M_{COEF(i)} = \min(\text{norm}_{(i,p)})$$

for p=−K to K.

The minimum norms of the electrodes are averaged by an appropriate weighted average algorithm (as above discussed). This yields the overall matching factor $M_{PACE(j)}$ for each pacing electrode Ep(j), i.e., $$M_{PACE(j)} = \frac{\sum M_{COEF(i)}}{n}$$

2. Symmetry Matching

Figure 7A:
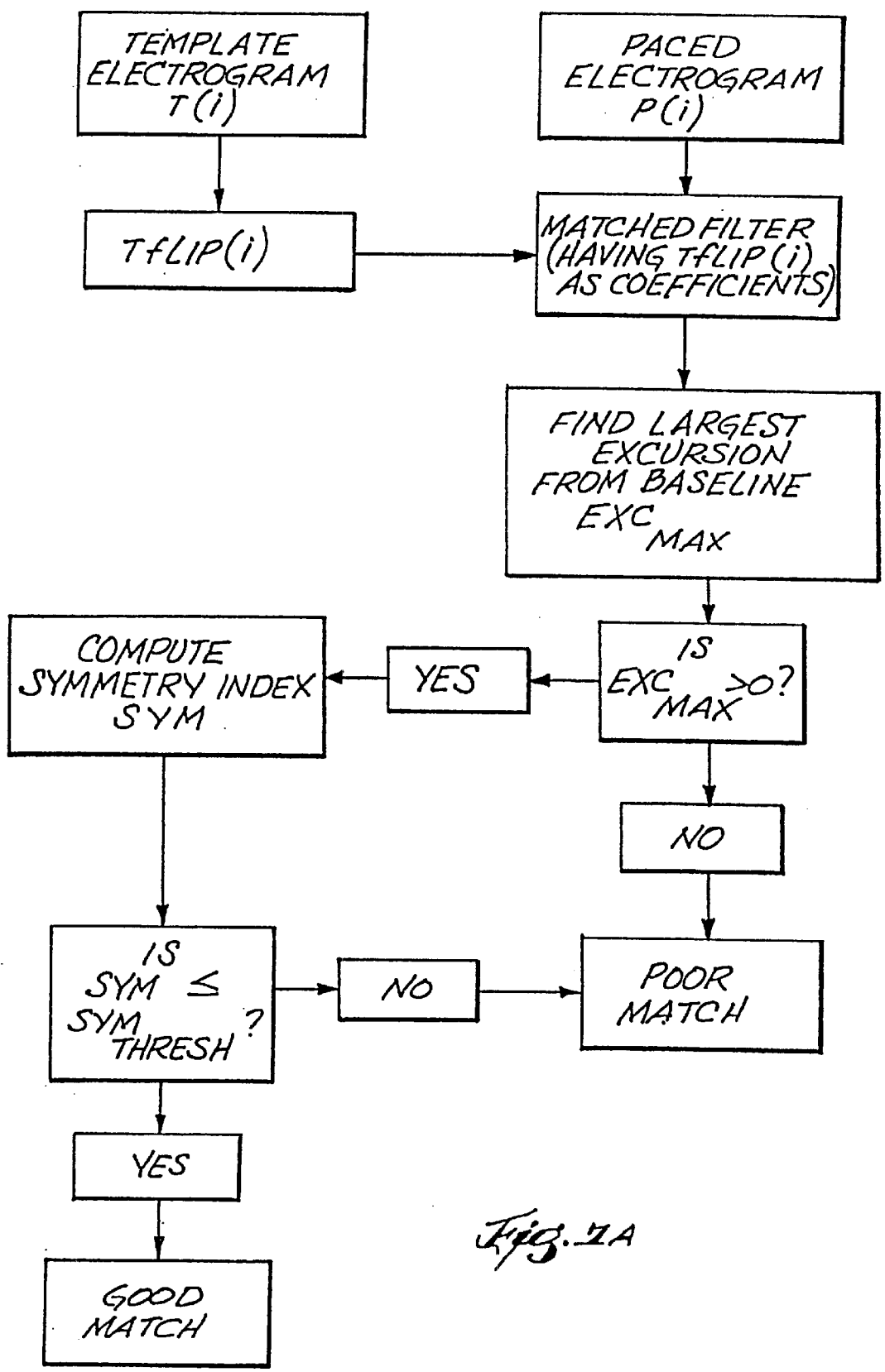

FIG. 7A shows a symmetry matching technique that embodies features of the invention.

The symmetry matching technique matched filters the paced electrogram P(i) for each electrode E(i) using Tflip(i) as coefficients of the matched filter. Each filter output is tested with respect to the largest excursion or extreme from baseline ($EXC_{MAX}$), the sign (positive or negative) of $EXC_{MAX}$, and a symmetry index (SYM), where:

$$SYM = \frac{\sum_{i=1}^{N} |PEAK_{CENTER-i} - PEAK_{CENTER+i}|}{\sum_{i=1}^{N} |PEAK_{CENTER-i}| + |PEAK_{CENTER+i}|}$$

except when $EXC_{MAX} < 0$, then SYM=1;

where N equals the number of local extremes to the left of $EXC_{MAX}$ (which is also equal to the number of local extremes situated to the right of $EXC_{MAX}$ (see FIG. 7B).

The technique first determines whether $EXC_{MAX} > 0$ (that is, whether it is positive). If $EXC_{MAX}$ is not positive (i.e, SYM=1.0), the technique deems that a poor match has occurred on this criteria-alone. If $EXC_{MAX}$ is positive, the technique goes on to compute the symmetry index SYM and compares SYM to a symmetry threshold ($SYM_{THRESH}$). If $SYM < SYM_{THRESH}$, the technique deems that a good match has occurred. In the preferred embodiment, $SYM_{THRESH} = 0.2$ (for perfect symmetry, SYM=0.0).

Similar electrograms will create a matched filtered output having a positive largest excursion. As the degree of similarity between the two electrograms increases, the matched filtered output will become increasingly more symmetric about this positive absolute maximum. The scoring factor is created for each electrogram comparison, where the scoring factor $M_{COEF(i)}=1=SYM$. The scoring factors based upon SYM are converted to an overall matching factor $M_{PACE(j)}$ for each pacing electrode Ep(j), as previously described. The pacing electrode Ep(j) creating the highest overall matching factor is designated to be close to a potential ablation site.

For example, FIG. 6E shows the matched filtered output MT(i) of the template electrogram of FIG. 6B and its left-to-right flipped counterpart of FIG. 6C. The electrogram of FIG. 6B is, in effect, matched filtered against itself, and the symmetry matching technique detects this. FIG. 6E shows a largest excursion that is positive and an output that is perfectly symmetric about the positive absolute maximum. A perfect scoring factor $M_{COEFC(i)}$ of 1.0 would be assigned.

Refer now to FIG. 6D, which is the matched filtered output MP(i) of the electrogram of FIG. 6A and the flipped template in FIG. 6C. These are different, yet similar electrograms. The symmetry matching technique detects this close similarity. FIG. 6D shows a positive largest excursion, and the output is relatively symmetric about this positive absolute maximum. A good scoring factor $M_{COEF(i)}$ of, for example, 0.9 would be assigned.

Figure 8A:
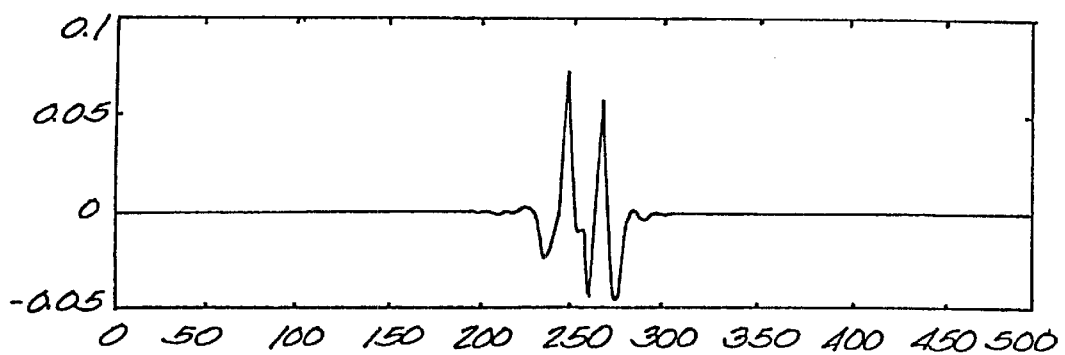
FIGS. 8A to 8C are representative electrogram morphologies processed in accordance with the symmetry matching technique shown in FIG. 7A.
Figure 8B:
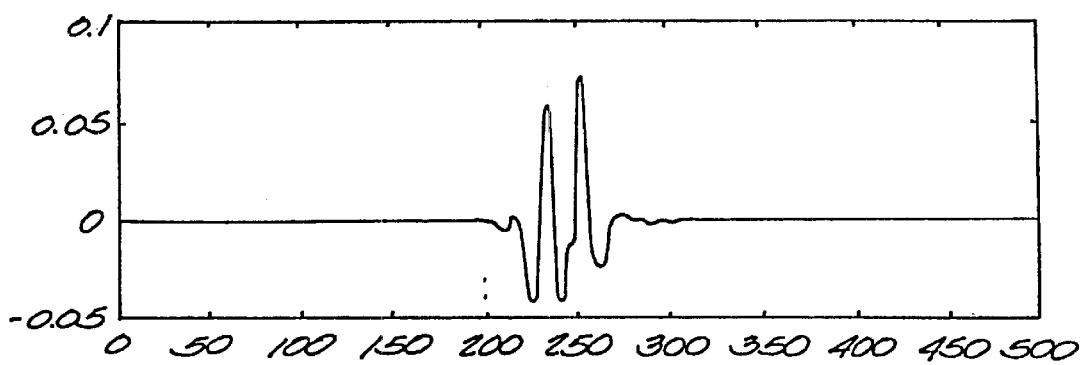
Figure 8C:
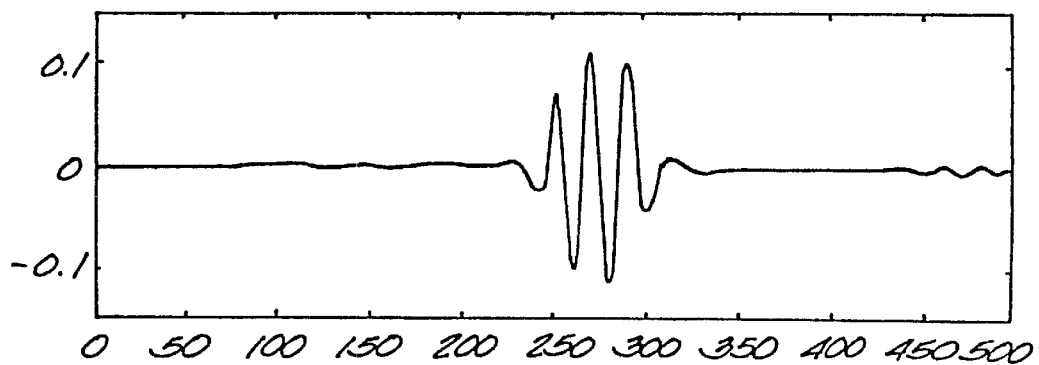

Refer now to FIG. 8C, which is the matched filtered output of the electrogram of FIG. 6A using the flipped template shown in FIG. 8B as coefficient of the matched filter. It can be seen that the electrogram shown in FIG. 8A has a morphology quite different than that shown in FIG. 6A. The symmetry matching technique detects this difference. FIG. 8C shows a negative largest excursion and an output that is not symmetric about this absolute maximum. A poor scoring factor $M_{COEF(i)}$ of zero would be assigned.

3. Matching Against Dirac Pulse

FIG. 9 shows a technique matching against Dirac pulse that embodies features of the invention.

This matching technique employs a whitening algorithm to first filter the template electrograms and the paced electrograms. The whitening filter transforms so-called colored noise, which can be 60-Hz (or 50-Hz) interference, or motion or muscular artifacts of the patient, to white noise.

The technique matched filters the whitened paced electrogram for each electrode using the left-right flipped, whitened template for that electrode as coefficients of the matched filter. Ideally, exactly matched, whitened electrograms will produce an output that equals a Dirac pulse. Therefore, each filter output is compared to a Dirac pulse. An algorithm scores the similarity for each electrode.

The pacing electrode whose whitened, matched filtered output most closely resembles a Dirac pulse is designated to be close to a potential ablation site.

4. Cross Correlation Technique

Figure 10:
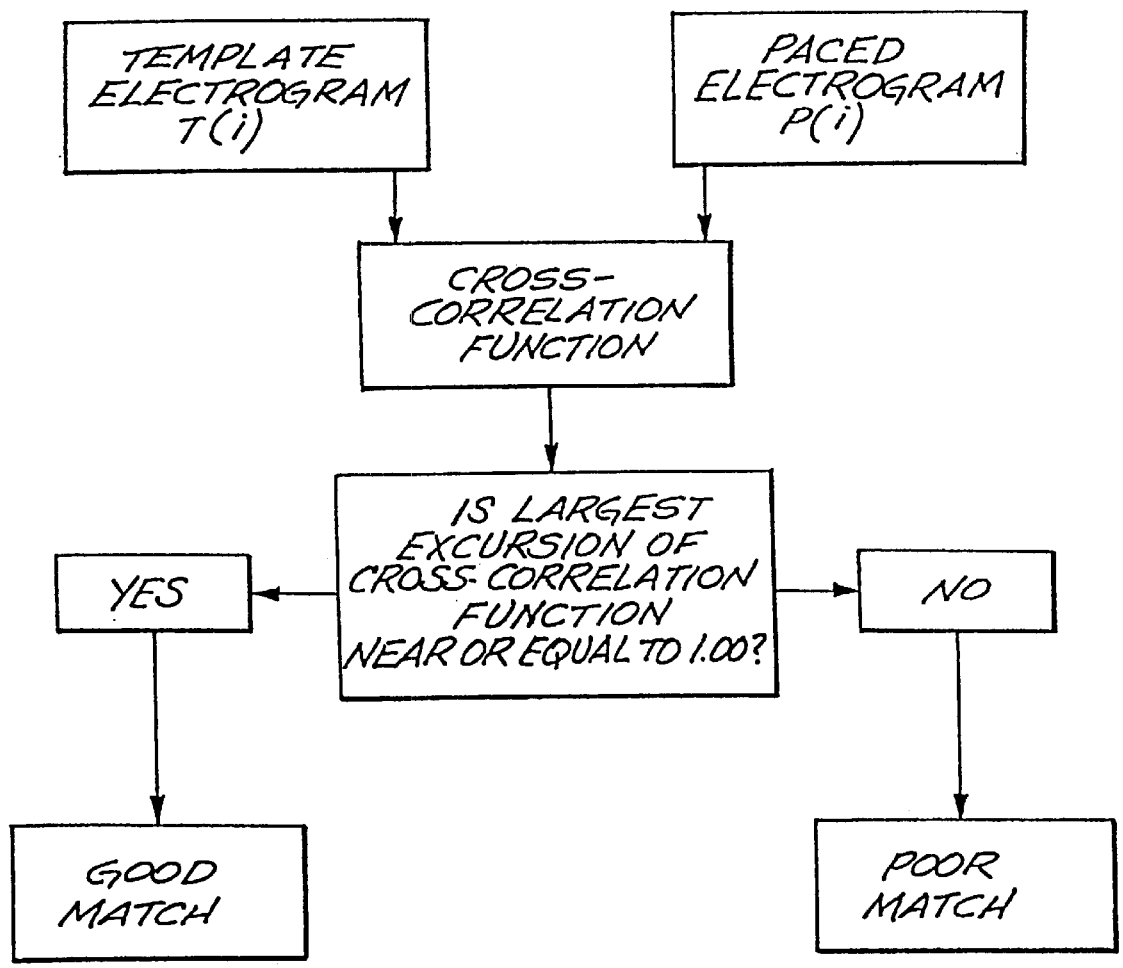
FIG. 10 is a flow chart showing a cross correlation coefficient technique that the process controller shown in FIG. 4A can employ for matching electrograms according to the invention.

FIG. 10 shows a cross correlation technique that embodies features of the invention.

This technique uses an appropriate algorithm to calculate for each electrode the cross correlation function between the template electrogram and the paced electrogram. For identical electrograms, the largest excursion of the cross correlation function will equal 1.0.

Various conventional methods for determining the cross correlation function can be used. For example, for M pairs of data {x(m), y(m)}, where x(m) is the template electrogram and y(m) is the paced electrogram, the correlation function can be calculated as follows:

$$rxy(k) = \frac{\sum [x(m) - x][y(m+k) - y]}{\sqrt{\sum [x(m) - x]^2 \sum [y(m) - y]^2}}$$

where m=1 to M; $-M \leq k \leq M$, and x and y are the means of the sequences {x} and {y}.

$M_{COEF(i)}$ is equal to the largest excursion of the sequence {rxy(k)} computed for the individual electrode E(i) (i.e., the largest excursion can be either negative or positive, depending upon the degree of intercorrelation).

The pacing electrode Ep(j) having an overall matching factor $M_{PACE(j)}$ closest to 1.0 is designated to be close to a potential ablation site. Additional information may be contained in the shift parameter k for each electrode.

Figure 11A:
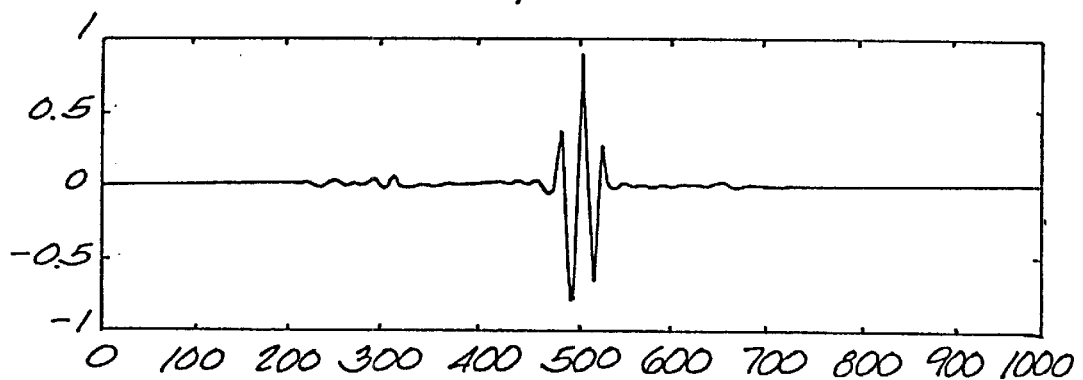
FIGS. 11A and 11B are representative electrogram morphologies processed in accordance with the cross correlation coefficient technique shown in FIG. 10.

For example, FIG. 11A shows the cross correlation function for the electrograms of FIG. 6A and FIG. 6B. These electrograms are quite similar, and the cross correlation technique detects this. The largest excursion of the cross correlation function in FIG. 11A is near 1.0 (i.e., it is 0.9694).

Figure 11B:
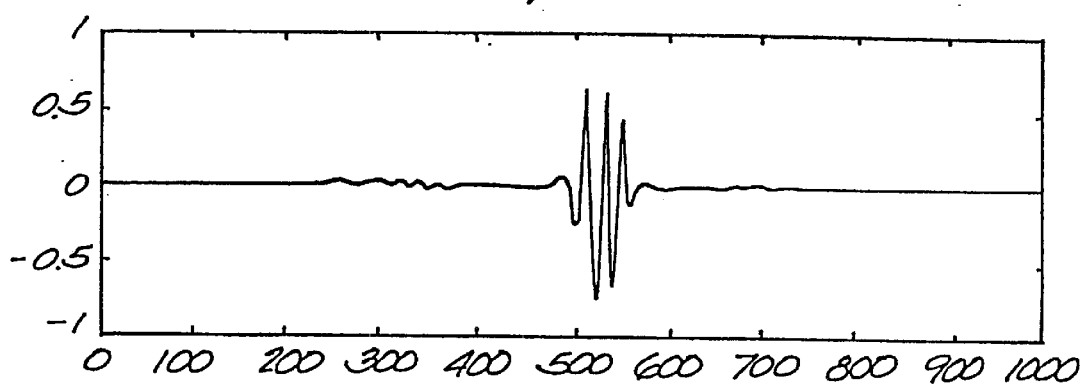

Refer now to FIG. 11B, which shows the cross correlation function for the unlike electrograms shown in FIGS. 6A and 8A. The cross correlation technique detects this lack of similarity. The largest excursion in FIG. 11B is negative (i.e., it is -0.7191).

5. Norm of the Difference Technique

Figure 12:
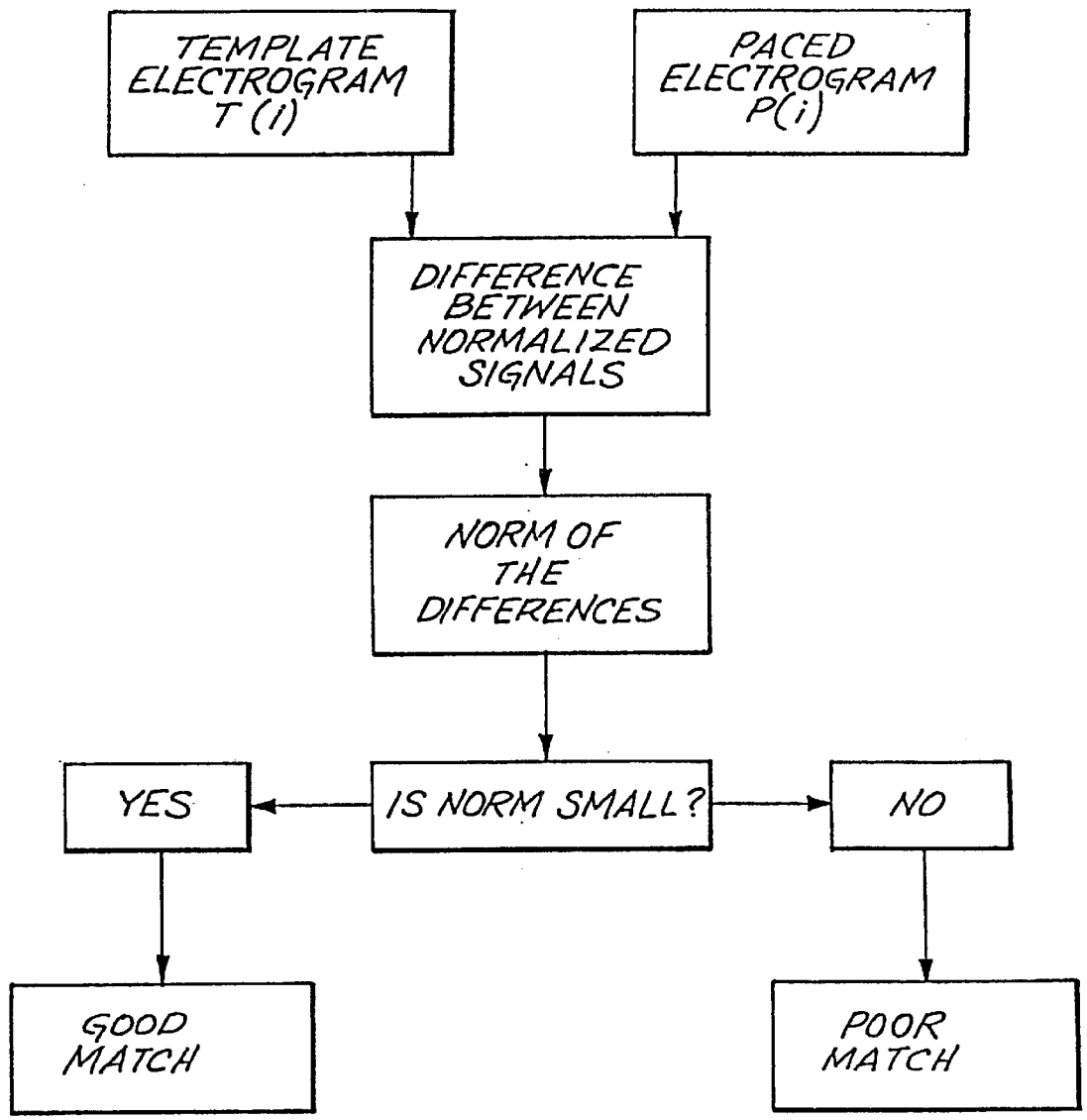
FIG. 12 is a flow chart showing a norm of the difference technique that the process controller shown in FIG. 4A can employ for matching electrograms according to the invention.

FIG. 12 shows a norm of the difference technique that embodies features of the invention.

This technique normalizes, for each electrode, the template electrogram with respect to the absolute value of its largest. excursion from baseline. This technique also normalizes, for each electrode, the paced electrogram with respect to the largest excursion from baseline. The technique then calculates, for each electrode, the norm of the difference between the template electrogram and the paced electrogram. The norm will decrease in proportion to the similarity of the electrograms.

Figure 13A:
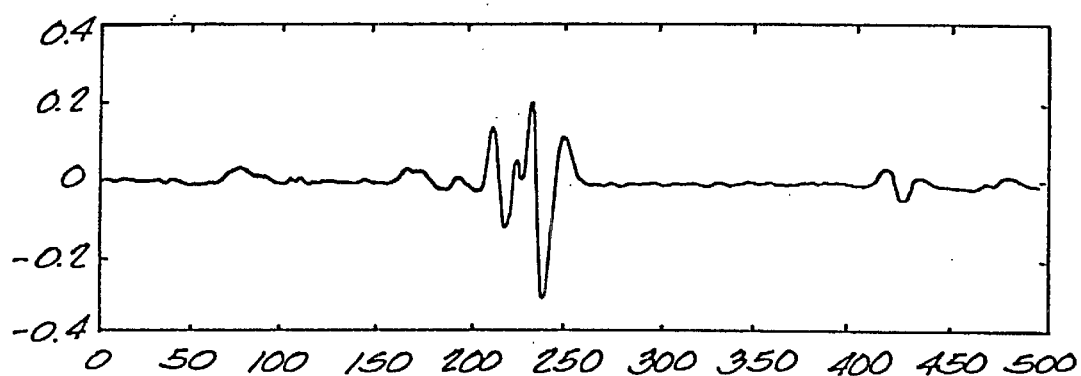
FIGS. 13A and 13B are representative electrogram morphologies processed in accordance with the norm of the difference technique shown in FIG. 12.

For example, FIG. 13A is the difference between the similar electrograms shown in FIGS. 6A and 6B, after each was normalized with respect to its largest excursion. This technique detects the At similarity with a relatively small norm of the difference (i.e., it is 0.9620).

Figure 13B:
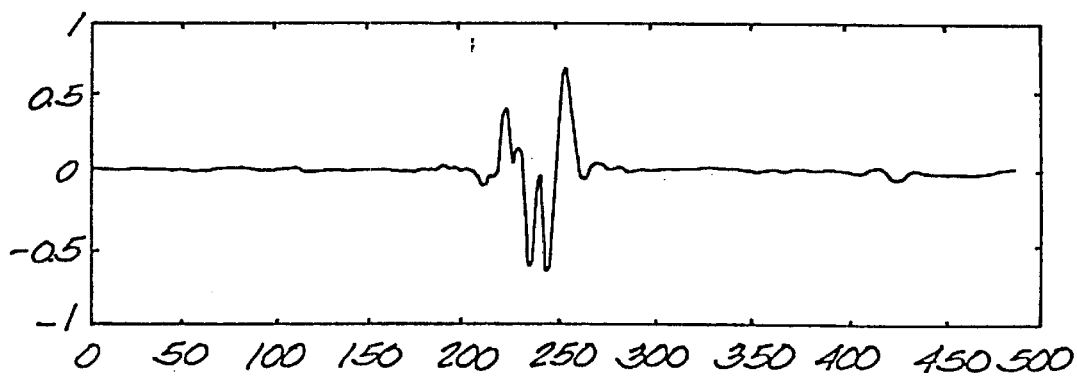

Refer now to FIG. 13B, which is the difference between the dissimilar electrograms shown in FIGS. 6A and 8A, after each was normalized with respect to its largest excursion. This technique detects the lack of similarity with a relatively high norm of the difference (i.e., it is 2.4972).

The technique preferably uses a weighted averaging algorithm to average, for each pacing electrode, the norm of the differences for all recording electrodes. The pacing electrode having the smallest average norm of the differences is designated the appropriate place to ablate.

The electrograms may or may not be filtered before analysis. A 1 to 300 Hz bandpass filter may be used for filtering. If a filter is used to reduce the noise for an electrogram that is used as a template, the same filter must also be used for the paced electrograms, since filtering may alter the electrogram morphology.

The electrograms might need to be aligned prior to processing. Any columnar alignment technique can be used. For example, the electrograms could be aligned about the point of largest positive slope.

The implementation of the system 10 described herein is based largely upon digital signal processing techniques. However, it should be appreciated that a person of ordinary skill in this technology area can easily adapt the digital techniques for analog signal processing.

The output signal y(t) of an analog matched filter is given by the analog convolution:

$$y(t)=x(t)*\text{Tflip}(t);$$

where Tflip(t)=EG(T−t), which constitutes a left-right flipped replica of the electrogram template EG(t) that has the period T.

Physically, an analog matched filter can be implemented with analog. integrators and adders. Also, optical realizations of such filters can be implemented, for example, by using optical slots to represent the template. After optical conversion, the input signal is passed through the optical slot. The average light intensity behind the optical slot plane is maximal when the shape of the optically converted input signal matches the shape of the slot. An optical sensor can measure the average light intensity and output a signal that represents the matched coefficient $M_{COEF(i)}$.

C. Location Output Isolation and Verification

In one implementation, the host processor 52 sets a match target $N_{Match}$, which numerically establishes a matching factor $M_{PACE(j)}$ at which a high probability exists that the pacing electrode is close to a potential ablation site. In a preferred implementation, NOTCH=0.8. When $M_{PACE(j)}$ > $N_{MATCH}$, the host processor 52 deems the location of the pacing electrode Ep(j) to be close to a potential site for ablation. When this occurs (as FIG. 4 shows), the host processor 52 transmits a SITE signal to an associated output display device 54 (see FIG. 1A). Through visual prompts, the display device 54 notifies the physician of the location of the pacing electrode Ep(j) and suggests that the location as a potential ablation site. When more two or more $M_{PACE(j)}$ > $N_{MATCH}$, the host processor 52 sorts to locate the $M_{PACE(j)}$ having the highest value. In this instance, the host processor 52 deems the pacing electrode Ep(j) with the highest $M_{PACE(j)}$ to be the one having the highest likelihood for being close to a potential ablation site and transmits the SITE signal accordingly.

In the illustrated and preferred embodiment, the process controller 32 provides iterative pacing and matching using different pacing and matching techniques. Using different pacing-and-compare techniques allows the comparison of the location output from one technique with the location output from one or more different techniques. Using iterative pacing and matching, the process controller 32 and the host processor 52 confirm and cross-check the location output to verify its accuracy before ablation. The host processor 52 can also rely upon alternative diagnostic techniques to analyze the biopotential morphology.

In the illustrated and preferred embodiment (see FIG. 1B), the system 10 also includes a roving pacing probe 68 usable in tandem with the basket structure 20 to generate and verify the location output.

1. Iterative Pacing

In the illustrated and preferred embodiment (see FIG. 1B), the process controller 32 includes a module 60 that allows the physician to select among different types of pacing techniques. The different pacing techniques allow the physician to conduct both global and localized site identification, with and without inducing the abnormal cardiac event.

At least one technique is appropriate for pacing a large tissue region to identify a subregion close to a potential ablation site, without the need to induce an abnormal cardiac event. In a preferred implementation, the process controller 32 first conditions the pacing module 48 in the mode to conduct pace mapping. Pace mapping uses all electrodes 24 on the structure 20 in sequence as the pacing electrode, and does not induce the cardiac event. Based upon pace mapping, the process controller 32 obtains a location output that points to a general subregion that is close to a potential ablation site.

Once the general region is identified, another pacing technique can be employed to more narrowly define the location of the potential ablation site within the general region. In a preferred implementation, the process controller 32 conditions the pacing module 48 in the matching mode to carry out entrainment or reset pacing, using the electrodes in the general subregion as the pacing electrodes. Entrainment or reset pacing in this subregion overdrives the arrhythmia, and provides enhanced differentiation of slow conduction zones. The process controller 32 thereby obtains a location output that is more localized with respect to the potential ablation site.

2. Iterative Matching

In the illustrated and preferred embodiment (see FIG. 1B), the process controller 32 also includes a module 62 that allows the physician to select more than one matching technique during iterative pacing. For example, the process controller 32 may, during pace mapping or entrainment/reset pacing, compare the templates to the paced electrograms by first pattern matching, then by symmetry matching, and then by norm of the difference. In this way, the process controller 32 determines the uniformity of the location output among the different matching techniques. The correspondence of the location outputs confirms their reliability.

3. Cross-Check Using Alternative Diagnostic Techniques

In the preferred embodiment, the process controller 32 is also electrically coupled by a bus 64 to a diagnostic module 66. Under the control of the process controller 32, as selected by the physician, the diagnostic module 66 conducts one or more alternative analyses of heart activity to cross check or verify the output location that the process controller 32 generates based upon electrogram matching.

In the illustrated embodiment (see FIG. 1B), the module 66 determines the fractionation of the paced electrograms. The degree of fractionation can be used as a cross-check that the physician can employ to cross-check and verify the output location or locations that the process controller 32 yields when operated in the matching mode.

4. The Roving Pacing Probe

Using the above iterative pacing and matching techniques, the location output may comprise a single electrode 24 or several electrodes 24 in a localized region of the structure 20. In the illustrated and preferred embodiment (see FIG. 1B), the system 10 further includes a roving pacing probe 68 that can be deployed in the heart region 12 while the multiple electrode structure 20 occupies the region 12. The roving probe 68 is electrically coupled to the pacing module 48 to emit pacing signals.

In use, once the process controller 32 generates the output location or locations using the elec-trodes 24 to pace the heart, the physician positions the roving electrode probe 68 within the localized region near the output location electrode or electrodes 24. The process controller 32 preferably includes a homing module 70 to aid the physician in guiding the roving electrode probe 68 in the localized region within the structure 20. Systems and methods for operating the homing module 70 are disclosed in copending patent application Ser. No. 08/320,301, filed Oct. 11, 1994, and entitled "Systems and Methods for Guiding Movable Electrode Elements Within Multiple Electrode structures", which is incorporated herein by reference.

The process controller 32 conditions, the pacing module 48 to emit pacing signals through the roving pacing probe 68 to pace the heart in the localized region, while the electrodes 24 record the resulting electrograms. By pacing this localized region with the roving pacing probe 68, while comparing the paced electrograms with the templates, the process controller 32 provides the capability of pacing and comparing at any location within the structure 20. In this way, the process controller 32 generates as output a location indicator that locates a site as close to a potential ablation site as possible. Of course, iterative pacing and matching techniques, as above described, can be practiced using the roving pacing probe 68.

Due to the often convoluted and complex contours of the inside surface of the heart, the basket structure 20 cannot contact the entire wall of a given heart chamber. The preferred implementation of the system 10 (as FIG. 1B shows) therefore deploys the roving pacing probe 68 outside the structure to pace the heart in those wall regions not in contact with the electrodes 24. The roving pacing probe 68 can also be deployed while the basket structure 20 occupies the region 12 to pace the heart in a different region or chamber. In either situation, the electrodes 24 on the structure 20 record the resulting paced electrograms for comparison by the process controller 32 to the templates. The process controller 32 is thus able to generate an output identifying a location close to a potential ablation site, even when the site lies outside the structure 20 or outside the chamber that the structure 20 occupies.

Acting upon the location output generated in accordance with the invention, the physician deploys the ablation electrode 36 to the location of the pacing electrode Ep(j) to conduct the ablation (as FIG. 1A shows). The homing module 70 (as already described and as shown in FIG. 1B) can also be used to aid the physician in deploying the ablation electrode 36 to the designated site, as disclosed in copending patent application Ser. No. 08/320,301, filed Oct. 11, 1994, and entitled "Systems and Methods for Guiding Movable Electrode Elements Within Multiple Electrode Structures", which is incorporated herein by reference.

It should be appreciated that the system 10 is not limited to the diagnosis and treatment of arrhythmia events. The system 10 can be used in the sampling mode, for example, to create templates while the heart is in sinus rhythm. In the matching mode, the heart can be paced at sinus rhythm rates and the paced electrograms compared to the templates to detect abnormal activation patterns associated with other forms of heart disease or to identify the presence of accessory pathways.

D. Time-Sequential Analysis

In the illustrated and preferred embodiment, the template electrograms at all electrodes 24 are recorded during the same time interval. Likewise, the pacing electrograms for each pacing electrode Ep(j) are recorded at all electrodes 24 during the same time interval. This technique requires the process controller 32 to have parallel processing channels equal in number to the number of electrodes 24 conditioned to record the electrograms. For example, it is typically desired to record electrogram information from thirty-two (32) electrode pairs when analyzing monomorphic VT. When the electrograms are recorded over the same time interval, the process controller 32 must be capable of handling thirty-two (32) parallel channels of information.

In an alternative embodiment, the process controller 32 can be operated in a time-sequential recording mode. In this mode, the process controller 32 records electrograms, either to create a template or to create paced electrograms for matching, at different time intervals. In this mode, the process controller 32 consolidates the time-sequential electrograms for composite analysis, as if the electrograms were recorded during the same time intervals.

The time-sequential mode can be used when the waveshapes of the electrograms to be analyzed are generally the same during each heart beat. For example, monomorphic VT is characterized by such time-invariant electrogram waveshapes. The time-sequential mode allows the physician to condition the process controller 32 to record time invariant electrograms in numbers greater than the number of processing channels that the process controller 32 has.

For example, if the process controller 32 can only accommodate twenty (20) channels of data at a given time, the time-sequential mode nevertheless allows information from thirty-two (32) electrograms to be recorded and processed.

Figure 22A:
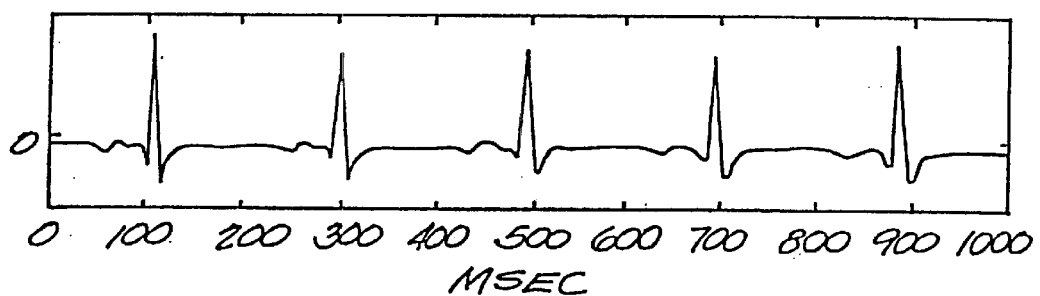
FIGS. 22A to 22D show representative individual electrograms taken at different time intervals during the time-sequential mode shown in FIG. 21, before time-alignment.
Figure 22B:
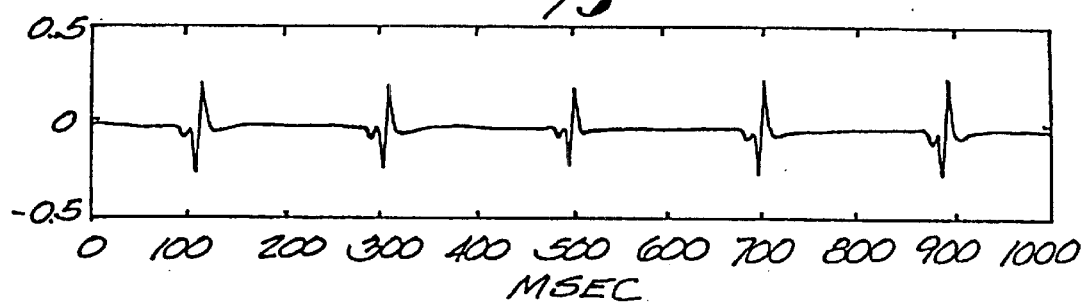

FIG. 21 shows the time-sequential mode of operation in diagrammatic flow chart form. During a first time interval TI(1)., the time-sequential mode simultaneously records electrograms at first electrode sites ES(1). In FIG. 21, the first electrode sites ES(1) number twenty (20) and are designated E(1) to E(20). The electrograms for the,first site electrodes E(1) to E(20) are retained for the first time interval TI(1). FIG. 22A shows representative electrograms recorded at E(1) during TI(1). FIG. 22B shows a representative electrogram recorded at E(2) during TI(1).

Figure 22C:
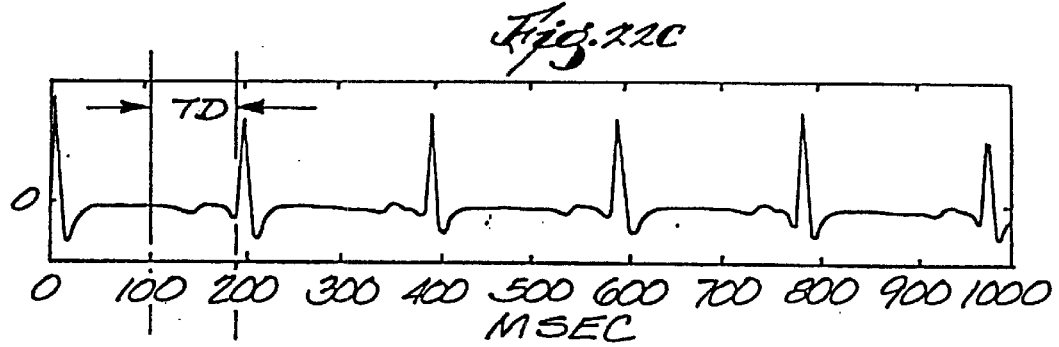
Figure 22D:
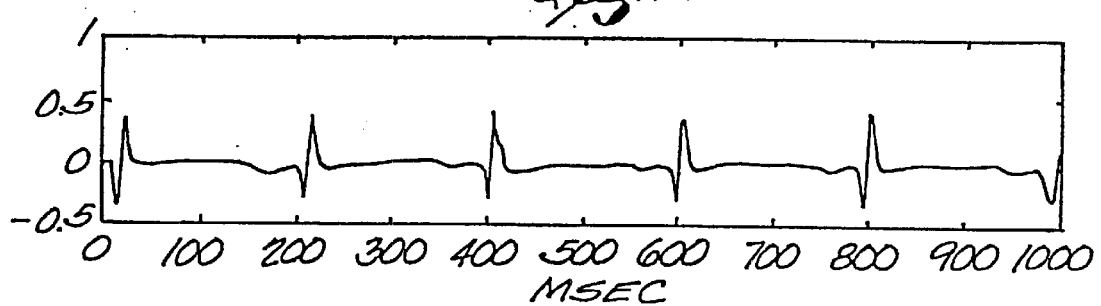

During a second time interval TI(2), the time-sequential mode simultaneously records electrograms at second electrode sites, at least one of which is an electrode site used during the first time interval TI(1). FIG. 21 identifies E(1) as the common electrode site. E(21) to E(32) comprise the remaining electrodes in ES(2). FIG. 22C shows representative electrograms recorded at the common electrode site E(1) during TI(2). FIG. 22D shows representative electrograms recorded at the additional electrode site E(21) during TI(2).

In a preferred implementation, the process controller 32 conditions the first electrode sites ES(1) for recording and records electrograms from these sites for TI(1)=4 seconds. The process controller 32 then automatically conditions the second electrode sites ES(2) for recording and records electrograms from these sites for TI(2)=4 seconds. Thus, over a time-sequenced interval of eight (8) seconds, the process controller 32 has recorded electrograms at thirty-two (32) electrode sites, which is the number desired for analysis.

The time-sequential mode determines the time difference TD between the electrograms for E(1) at TI(1) and TI(2). FIG. 22C shows TD.

Figure 23A:
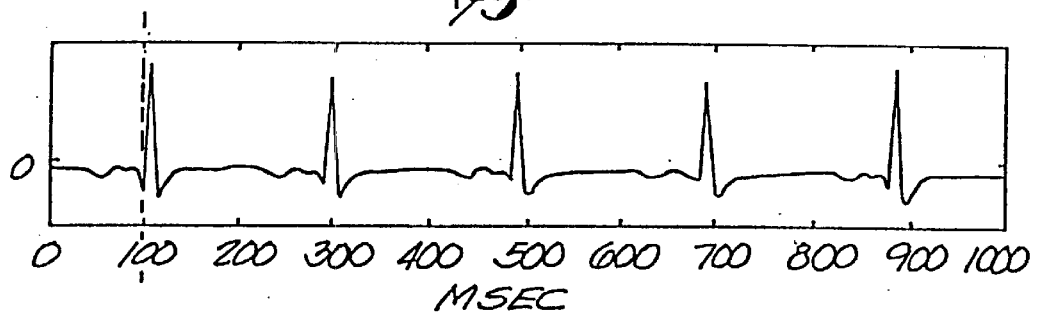
FIGS. 23A to 23D show the representative individual electrograms shown in FIGS. 22A to 22D, after time-alignment, to form the electrogram composite.
Figure 23B:
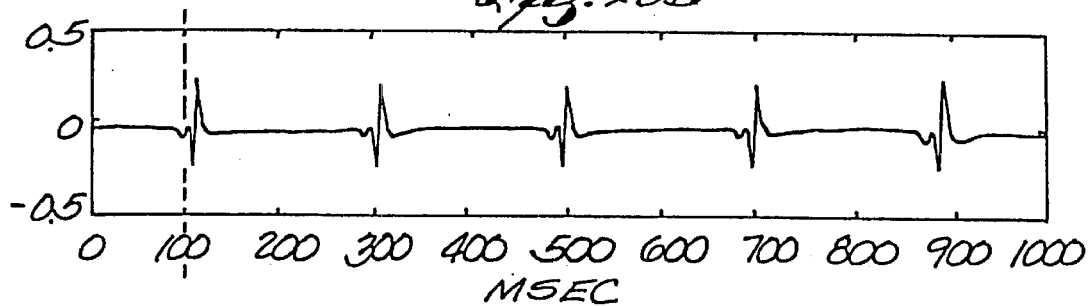
Figure 23C:
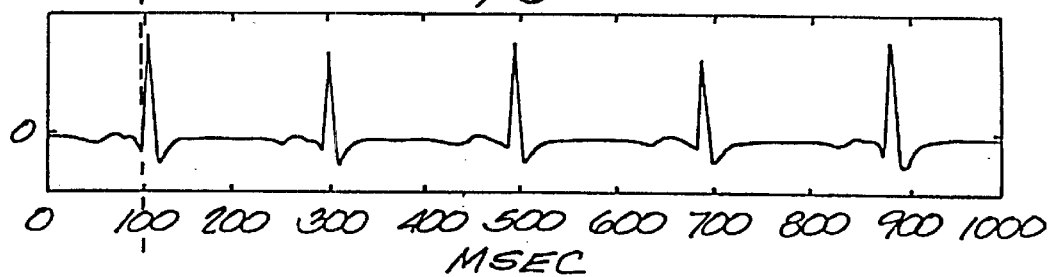

The time-sequential mode time-aligns E(1) at TI(2) with E(1) at TI(l) by left-shifting E(1) at TI(2) by TD. FIG. 23C shows the representative electrograms recorded at E(1) during TI(2) after time-alignment with the electrograms recorded at E(1) during TI(1), which are shown in FIG. 23A.

Figure 23D:
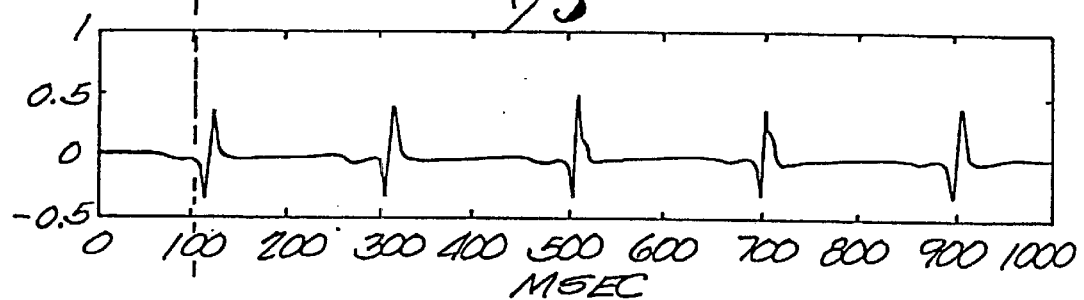

The time-sequential mode also left-shifts the electrograms E(21) through E(32) by the same amount TD. FIG. 23D shows the representative electrograms recorded at E(21) during TI(2) after time-alignment.

In this way, the time-sequential mode creates the electrogram composite EC, which consists of the time-registered electrograms E(1) to E(32) taken at TI(1) and TI(2). The time-alignment process of creating the electrogram composite EC can be done manually by the physician,. by interacting with the display device 54. Preferably, the host processor 52 automatically analyzes the signals, computes TD, and accomplishes the time-alignment to create the composite electrogram EC. Alternatively, TD need not be computed.

The physician or the operator can make use of any time-assignment method to align the signals based on the information contained in the common channels E(1). An example of useful information is the location of the maximal slopes of E(1). Of course, this algorithm can be automatically implemented and executed.

Though taken at different time intervals TI(1) and TI(2), the time-aligned electrogram composite EC can be analyzed in the same manner as electrograms taken simultaneously during the same time interval. In the context of the system 10 described herein, the electrogram composite EC can be used to create the electrogram template, or to create paced electrograms for comparison with an electrogram template, or as electrograms for any other diagnostic purpose.

For example, using the above described time-sequential methodology, virtually all types of signals derived from biological events. can be processed, such as electrocardiograms, tissue biopotential signals, pressure waves, electrogastrograms, electromyograms, electroencephalograms, impedance measurements, and temperature measurements.

II. Endocardially Paced Electrocardiograms

A. Electrocardiogram Matching

In the preceding embodiments, the endocardially positioned basket structure 20 both paces and senses the resulting electrograms. In an alternative implementation, the process controller 32 can condition the pacing module 48 in the sampling mode to pace the heart to induce a desired cardiac event, using individual or pairs of electrodes 24 on the basket structure 20 deployed in the heart region 12 (as already described), while creating templates of the resulting electrocardiograms recorded by the processing module 50 from body surface electrodes electrically coupled to the process controller 32.

In this implementation, during the matching mode, the process controller 32 paces the heart with the individual or pairs of endocardial electrodes 24 positioned on the structure 20 in the heart region 12. The resulting paced electrocardiograms are recorded by the same body surface electrodes (located in the same position as during the sampling mode) and compared to the electrocardiogram templates in the manner above described.

In this implementation, the process controller 32 generates the location output based upon comparing the electrocardiogram sample templates with endocardially paced electrocardiograms.

B. Electrocardiogram Time Delays

Endocardially paced electrocardiograms can also be used to identify regions of slow conduction.

In this implementation, while the process controller 32 conditions the pacing module 48 to pace the heart with the individual or pairs of electrodes 24 positioned on the structure 20 endocardially in the heart region 12, the resulting endocardially paced electrocardiograms are recorded by body surface electrodes coupled to the process controller 32. From the endocardially paced electrocardiograms, the process controller 32 measures the time difference between the pacing signal and the onset of the Q-wave to detect slow conduction regions (characterized by abnormally large time delays).

Preferably, the process controller 32 generates maps displaying iso-time delay regions based upon these endocardially paced electrocardiograms, to further aid in the location of the slow conduction region.

C. Characterizing Tissue Morphology

Time delays obtained from endocardially paced electrocardiograms can also characterize heart tissue morphology.

In this implementation, the body surface electrodes record electrocardiograms while the pacing module 48 paces the heart with the individual or pairs of electrodes 24 positioned on the structure 20 in the heart region 12. The pacing module 48 first paces the heart at or near normal sinus rhythm rates. The process controller 32 registers the time delays recorded from the resulting electrocardiograms. The pacing module 48 next paces the heart at an increased rate, e.g., at or near an arrhythmia rate. The process controller 32 registers the resulting time delays from the resulting electrocardiograms.

The process controller 32 compares the paced sinus rate time delays with the paced arrhythmia rate time delay. The location of the pacing electrodes where the time delays shortened as the pacing rate increased are near regions of healthy tissue. The location of pacing electrodes where the time delays lengthened as the pacing rate increased are near regions of ischemic tissue. The process controller 32 preferably generates iso-display maps showing the distribution of the time delay differences, thereby aiding the physician in differentiating between regions of healthy and ischemic tissue.

III. Pacing Artifact Removal

Pacing artifacts in the pacing electrograms may be eliminated by conventional techniques to better discern the initial point of depolarization. However, in the illustrated and preferred embodiment, the process controller 32 includes a filter 56 (see FIG. 4) that removes the pacing artifact for this purpose without otherwise altering the morphology of the electrogram. The operation of the filter 56 may vary.

A. Nonlinear Filter

Figure 14A:
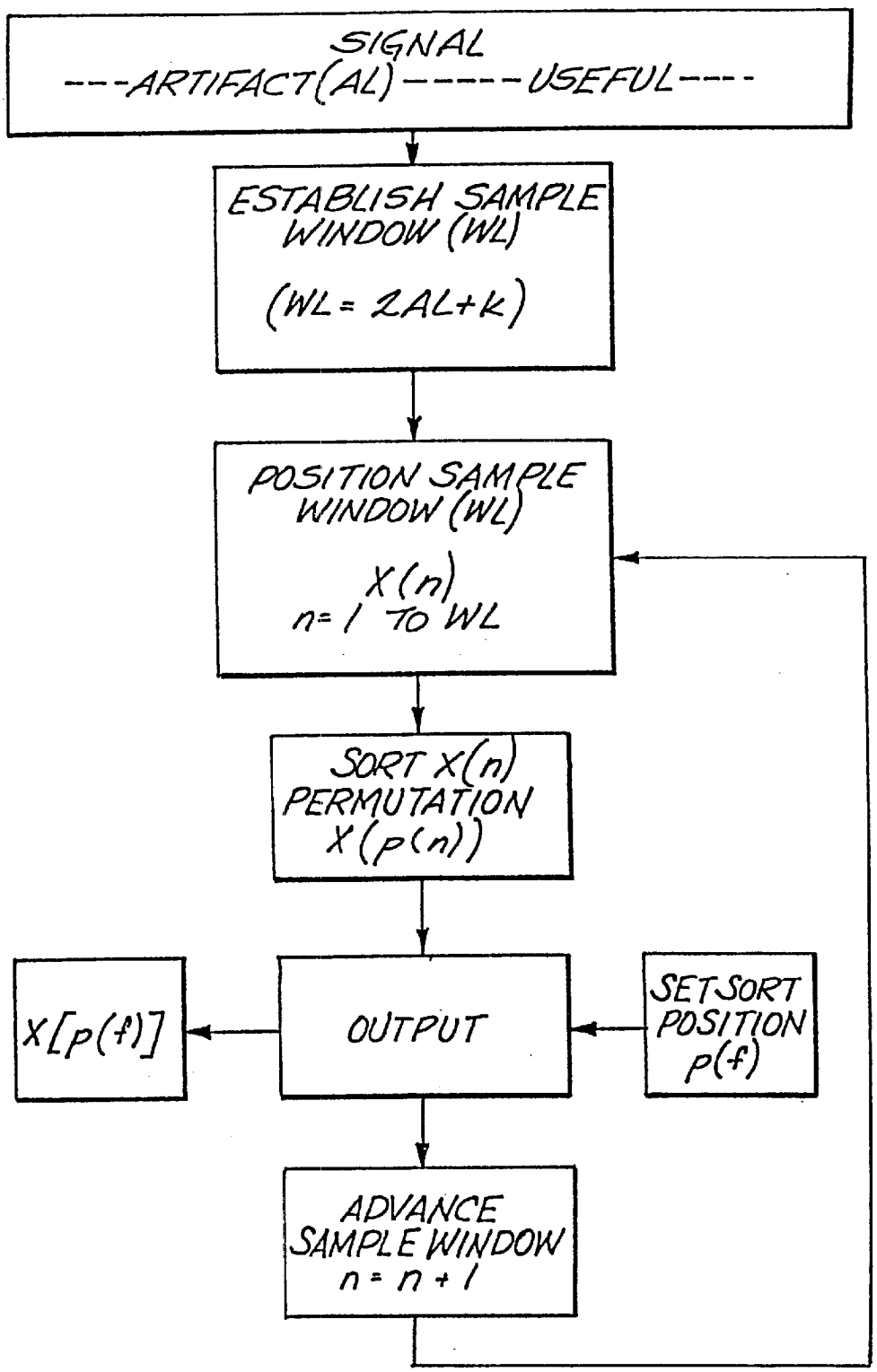
FIG. 14A is a flow chart showing a filtering technique that the process controller shown in FIG. 4A can employ for removing pacing artifacts according to the invention.

In the preferred embodiment, the filter 56 implements a nonlinear sorting algorithm of the type shown in FIG. 14A.

FIG. 14B shows a representative implementation and filter output for the algorithm in diagrammatic form.

The algorithm establishes a sample window. The sample window has a predetermined length (WL), expressed in terms of the number of discrete sample points the window contains. The predetermined length (WL) of the sample window takes into account the length (AL) of the pacing artifact, which is expressed in terms of the number of sample points that encompass the pacing artifact. Preferably, the window length WL is an odd number.

If WL is significantly smaller than twice AL, the sorting algorithm will not serve to eliminate the pacing artifact to the extent necessary to accurately discern the initial point of depolarization. There is, however, a limitation placed upon how large WL is relative to the size of AL. When WL is significantly larger than twice AL, the morphology of the electrogram will be distorted by being spread out with respect to time.

It is believed that the sample window length should preferably be at least twice the pacing artifact length. Most preferably, $WL \geq 2AL+k$, where k=1 to WL/2. k is an additive amount that optimizes the elimination of the artifact without time distortion.

The algorithm advances the sample window along the electrogram, taking a succession of boxcar samples, X(n), where n=1 to WL. The algorithm sorts the sample values X(n) in the window from smallest value to largest value. The sorted permutation is the sequence $\{X(p[n])\}$, where $\{p[n]\}$ is a permutation of $\{n\}$ resulting from the sorting process, and where n=1 to WL. The algorithm selects one of the sort positions p[f] according to prescribed criteria, where f=1 to WL. The selection criteria will be discussed in greater detail later.

The algorithm outputs the sample value X(p[f]) contained in the selected sort position, which constitutes the filter output for the boxcar sample. The algorithm outputs X(p[f]) and advances the window forward in time one sample point.

The algorithm repeats the sorting process, generating a filter output for each boxcar sample and advancing the window, until the entire electrogram has been processed. The algorithm then plots the filter outputs with respect to time, which constitutes the filtered electrogram.

EXAMPLE (Nonlinear Filtering)

For example, given WL=5, the sequence of samples values X(n) is:

The sequence of sample values X(1 to 5) constitutes the boxcar sample.

The algorithm sorts the sequence X(1 to 5) in increasing numerical value, or

X(2)<X(1)<X(5)<X(4)<X(3).

The algorithm establishes the sort positions p(n) based upon this permutation, or The algorithm selects a sort position p(f) according to prescribed criteria. The criteria for selecting the sort position takes into account the length of the artifact AL, as will be discussed later. In the preferred embodiment, the criteria specifies the sort position relative to the other sort positions. In this implementation, (f) is expressed as a position (z) of WL positions, i.e., p(z/WL), where WL is the size of the sort window. The position z is selected taking into account AL, and, more particularly, z should increase as AL decreases.

For example, for WL=5, if z=3, then p(3/5) means that X(p(3)) replaces x(3) in the output sequence. The value X(p(3)) is 6, which becomes the filter output for this boxcar sample, based upon the selected sort position criteria.

In this particular case, p(3/5) criteria actually implements a median filter. For a given window, the following sort position z constitutes the median $$z = \left[\frac{WL+1}{2}\right]$$

where:

$1 \leq z \leq WL$, and the expression:

$$\left[\frac{WL+1}{2}\right]$$

represents the integer part of:

For example [3.9]=3, just as [3.1]=3.

Further details on median filtering techniques are disclosed in "VLSI Array Processors" by S. Y. Kung (Prentice Hall, (1991).

Alternatively, if the selected sort position is p(4/5), the value X(p(4)) is 8, which becomes the nonlinear, non-median filter output for this boxcar sample, based upon the selected sort position criteria. This corresponds to x(4) of the output sequence.

The algorithm advances the window one sample at a time, sorting the sample enclosed within the window, and generating a filter output based upon the sort criteria, and so on until the entire electrogram has been filtered.

In the preferred embodiment, the algorithm keeps the timing of filter output in sequence with the timing of the electrogram by retaining the value of edge samples, so that the number of filter outputs equal the number of electrogram samples. The number of edge values retained, of course, depends upon the size of the sample window WL.

More particularly, the algorithm retains a prescribed number, $y_1$, of beginning sample values a number, $y_2$, of ending sample values, arranging the filter output between the prescribed number of beginning and ending sample values to keep the filter output arranged with respect to time in sequence with the derived biological signal. In the preferred implementation, $$y_1 = z-1$$

and $$y_2 = WL-z$$

FIG. 14B shows the filtering of ten sample points (4 2 7 5 1 10 3 8 9 6) in accordance with the above described technique. The window length WL in FIG. 14B is 5, and the 'sort criteria is median filtering, i.e. p(3/5). FIG. 14B shows the retention of the edge samples, two samples (4 and 2) at the front edge ($y_1 = z-1$ or 3−1=2) and two samples 9 and 6 at the rear edge ($y_2 = WL-z$ or 5−3=2). FIG. 14B also shows the filter outputs (4 5 5 5 8 8) between the edge samples, with the sorted samples appearing to the right of the filter outputs.

FIG. 14C shows the filtering of the same ten sample points (4 2 7 5 1 10 3 8 9 6), with the same window length WL of 5, but with a non-median sort criteria p(4/5). FIG. 14C shows the retention of the edge samples, three samples (4, 2, 7) in at the front edge ($Y_1 = z-1$ or 4−1=3) and one sample 6 at the rear edge ($Y_2 = WL-z$ or 5−4=1). FIG. 14C shows the filter output for the p(4/5)-criterion: (5 7 7 8 9 9) between the edge samples.

The selection of the sort position p(f) takes into account the morphology of the pacing artifact in terms of the length of the artifact AL, expressed in terms of the number of sample points that encompass it. The percentage value of f should increase as the artifact length AL decreases, or, given a constant WL, z should increase as AL decreases.

EXAMPLE (Sort Position Selection Criteria)

Figure 15A:
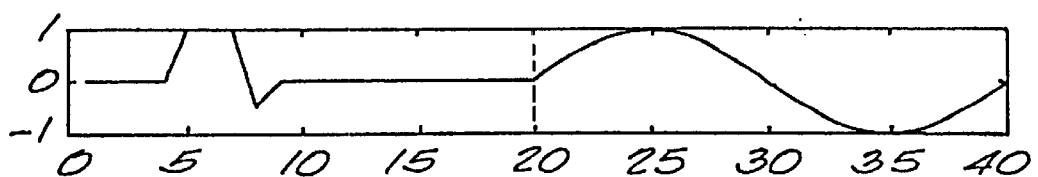
FIGS. 15A to D; 16A to D; 17A to D are representative electrogram morphologies showing the effect of the sort position selection criteria in removing the pacing artifact employing the technique shown in FIG. 14.
Figure 15B:
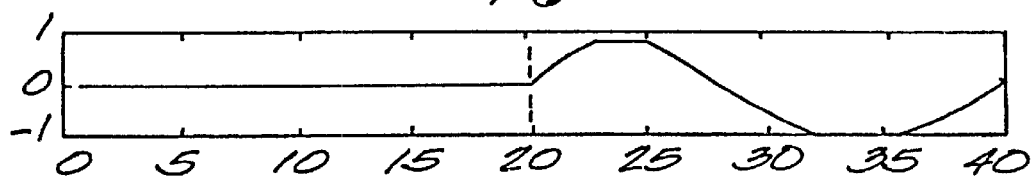
Figure 15C:
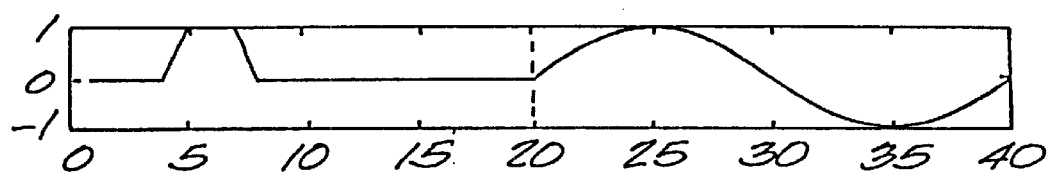
Figure 15D:
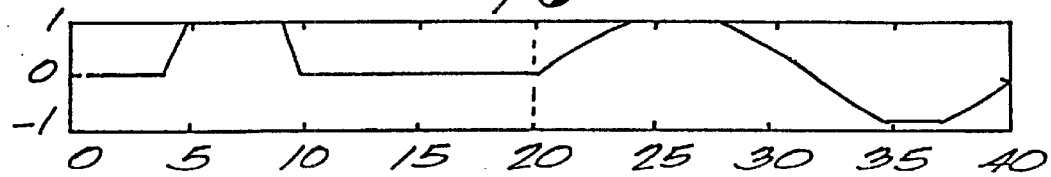
Figure 16A:
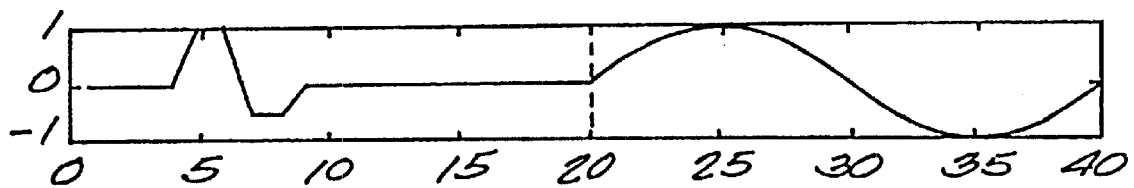
Figure 16B:
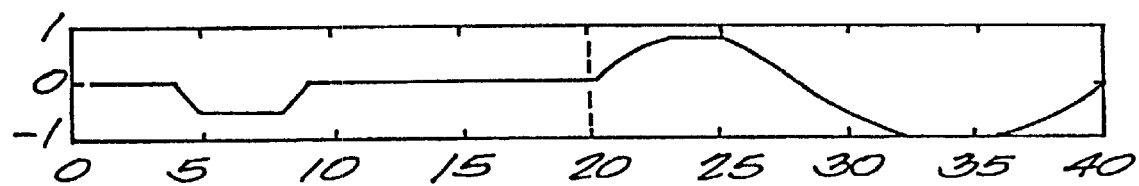
Figure 16C:
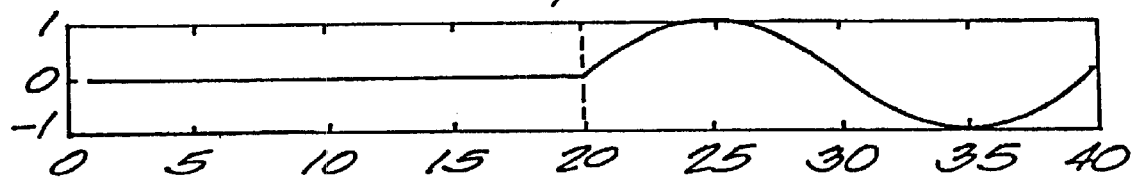
Figure 16D:
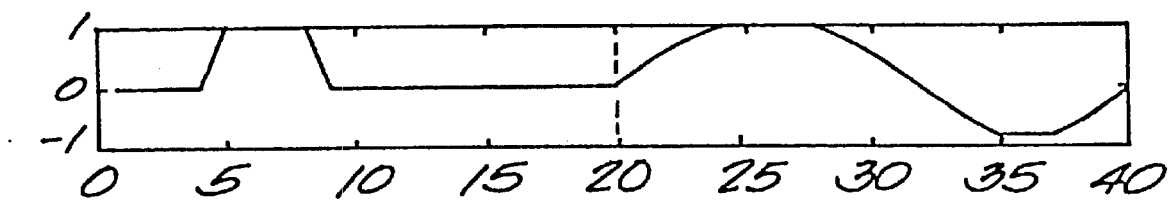

FIG. 15A shows a simulated pacing artifact where AL is 5 and the width of the highest peak is 3. FIG. 15B shows the filtered output for p(2/5); FIG. 15C shows the filtered output for the median, or p(3/5); and FIG. 15D shows the filtered output for p(4/5). The criteria p(2/5) fully eliminated the pacing artifact (FIG. 15B), whereas the criteria p(3/5) and p(4/5) did not (FIGS. 15C and 15D, respectively). Thus, the optimal elimination of certain pacing artifacts requires nonlinear, non-median filtering, where the position z comprises a positive integer; $1 \leq z \leq WL$; and:

FIG. 16A shows a simulated pacing artifact where AL is 5 and the width of the highest peak is 2. FIG. 16B shows the filtered output for p(2/5); FIG. 16C shows the filtered output for p(3/5), i.e. the median; and FIG. 16D shows the filtered output for p(4/5). The criteria p(3/5) fully eliminated the pacing artifact (FIG. 16C), whereas the criteria p(2/5) and p(4/5) did not (FIGS. 16B and 16D, respectively).

Figure 17A:
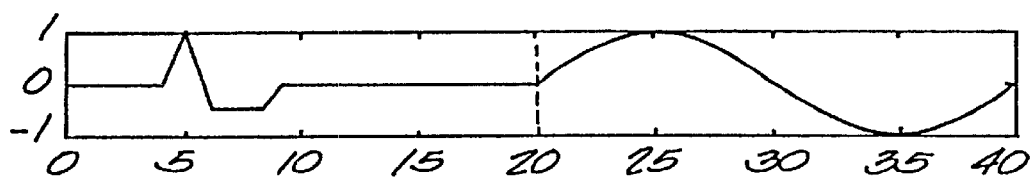
Figure 17B:
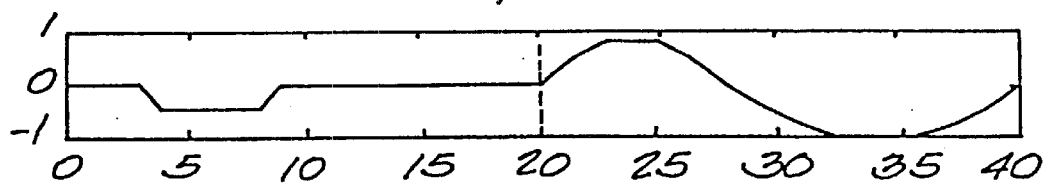
Figure 17C:
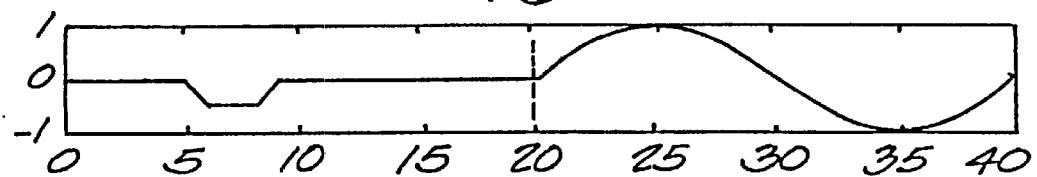
Figure 17D:
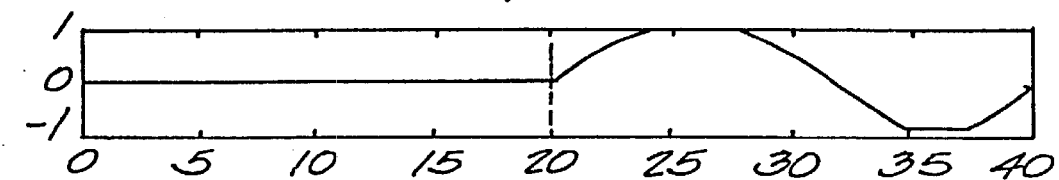

FIG. 17A shows a simulated pacing artifact where AL is 5 and the width of the highest peak is 1. FIG. 17B shows the filtered output for p(2/5); FIG. 17C shows the filtered output for p(3/5), i.e. the median; and FIG. 17D shows the filtered output for p(4/5). The criteria p(4/5) fully eliminated the pacing artifact (FIG. 17D), whereas the criteria p(2/5) and p(3/5) did not (FIGS. 17B and 17C, respectively).

Figure 18A:
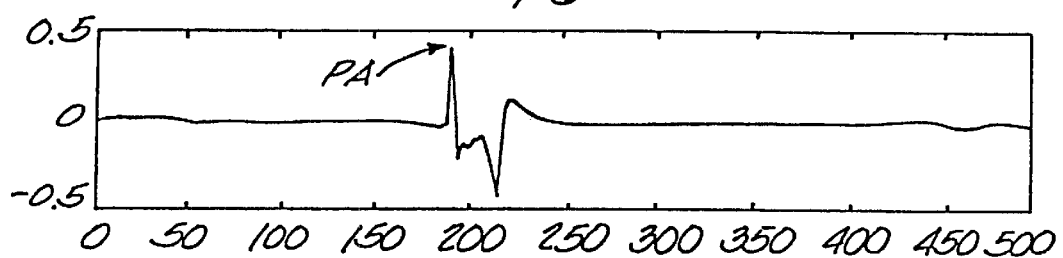
FIGS. 18A to C are representative electrogram morphologies showing the effect of the sample window size in removing the pacing artifact employing the technique shown in FIG. 14.

FIG. 18A shows a paced electrogram consisting of 500 samples taken in increments of 0.5 seconds. The designation PA in FIG. 18A marks the location of the pacing artifact, which is 5 sample periods in length (i.e., AL=5).

Figure 18B:
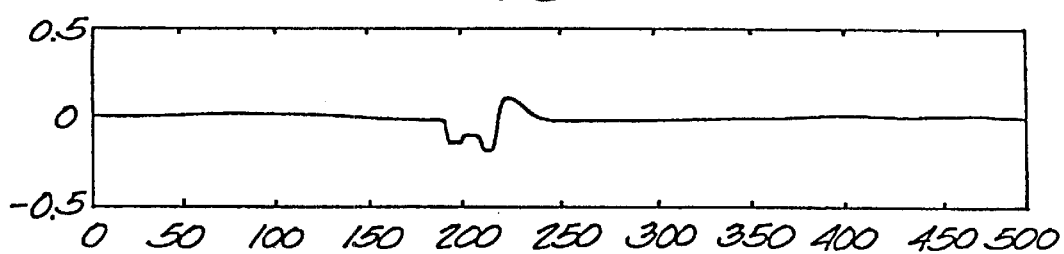
Figure 18C:
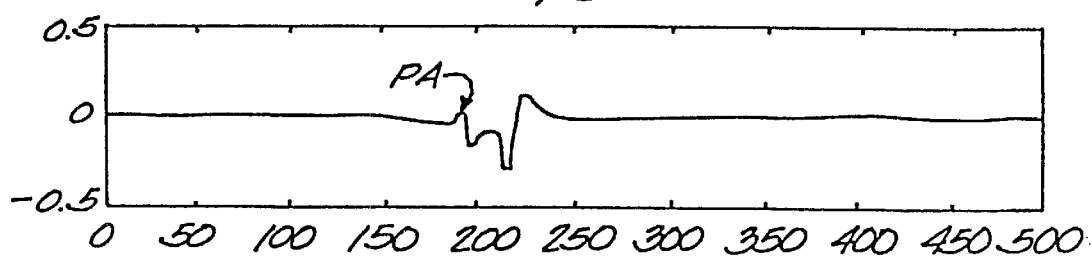

FIG. 18C shows a plot of the filter output generated by filtering the electrogram of FIG. 18A using a sample window size WL=7 (that is, less than twice the artifact sample size) and specifying the median p(4/7) as the sort position. FIG. 18C shows a reduction in the size but not an elimination of the pacing artifact PA by median filtering.

FIG. 18B shows a plot of the filter output generated by filtering, the electrogram of FIG. 18A using a sample window size WL=11. (that is, WL=2AL +1), while still specifying the median p(6/11) as the sort position. FIG. 18B shows an elimination of the pacing artifact by median filtering.

Except for the median filter p(3/5), the implementation of this type of nonlinear filter will distort both the positive and negative phases of the useful signal (see FIGS. 15B/D, 16B/D, and 17B/D.)

B. Adaptive Filtering

Figure 19:
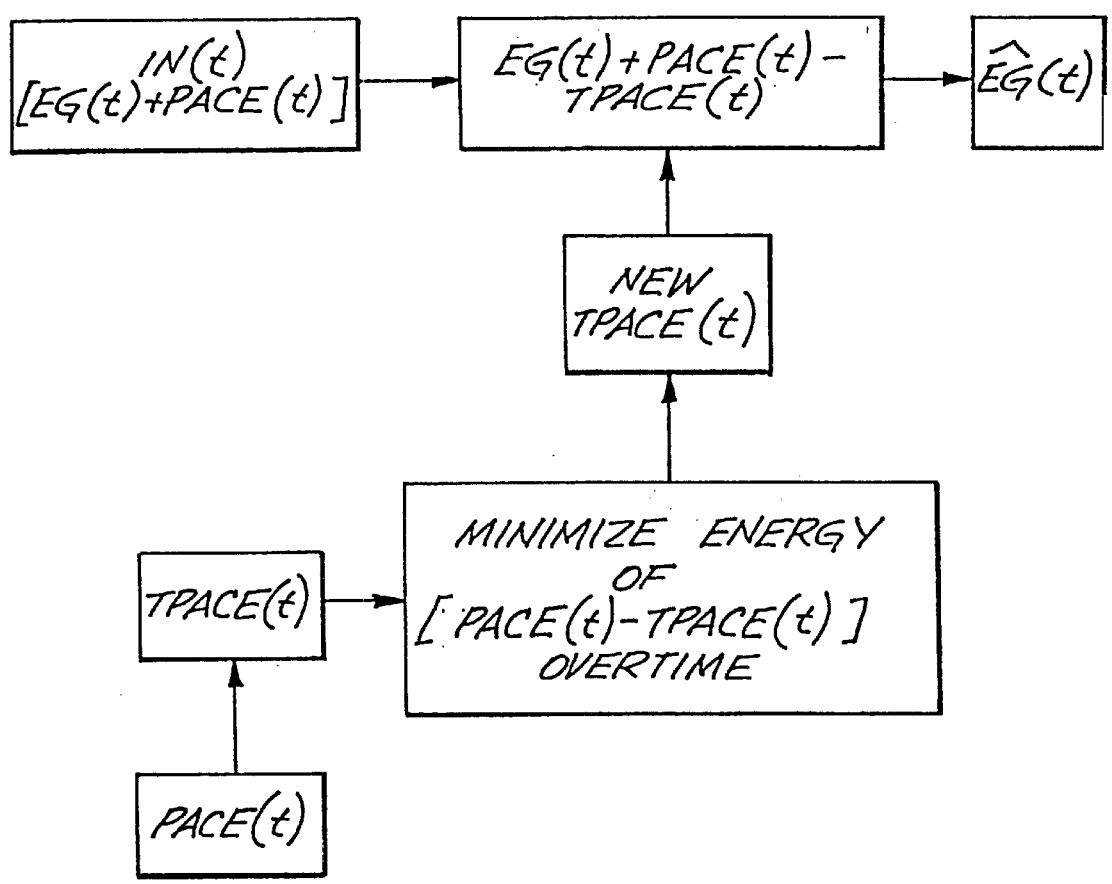
FIG. 19 is a diagrammatic view of an adaptive filtering technique that the process controller shown in FIG. 4A can employ for removing pacing artifacts according to the invention.

Alternatively, the filter 56 can implement the adaptive filtering algorithm shown in FIG. 19 to remove the pacing artifact.

The filter 56 generates an internal variable TPACE(t) expressing a template of the pacing artifact itself. The function TPACE(t) preferably begins with a preestablished template typical for a pacing artifact. Alternatively, the algorithm can create an initial template by manually selecting a window about the artifact and creating a template by, for example, conventional signal averaging techniques. This template could be adaptively updated using appropriate signal averaging techniques.

Figure 24:
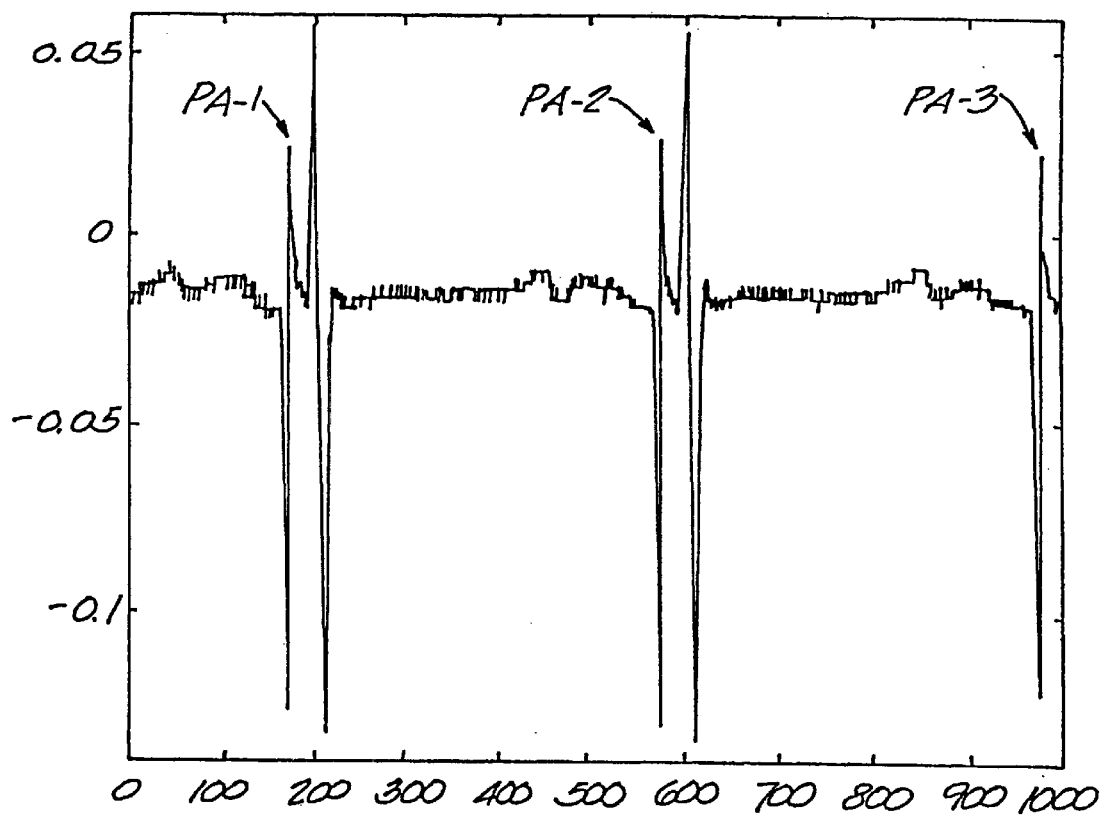
FIG. 24 shows a pace electrogram with three pacing artifacts, before adaptive filtering.

FIGS. 24 to 28 exemplify a preferred way of generating a template of the pacing artifact. FIG. 24 shows a portion of a recording of a paced electrogram extending over about two beats and a half. FIG. 24 shows three pacing pulses (PA-1; PA-2; PA-3), which are the artifacts that are to be ultimately removed. The physician preferably selects windows about each pacing pulse PA-1 to 3 to create an averaged template. Alternatively, the physician can select one of the pacing pulse, for example PA-1, to generate-the template.

Figure 25A:
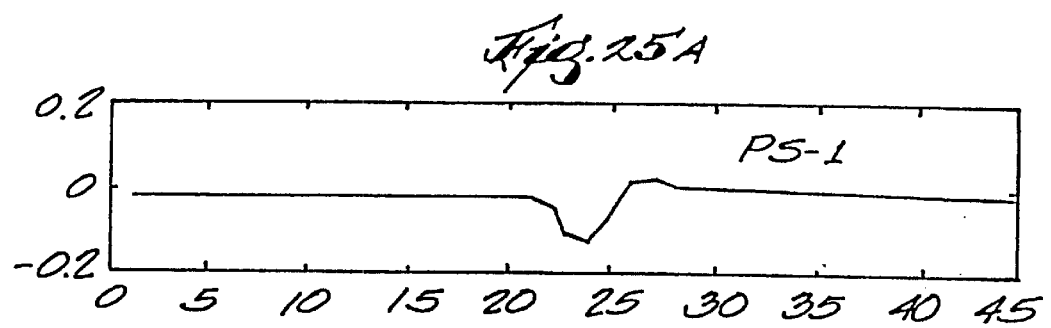
FIGS. 25A to C show the artifact signals of the three pacing artifacts shown in FIG. 24, manually selected by the physician, before alignment and truncation.
Figure 25B:
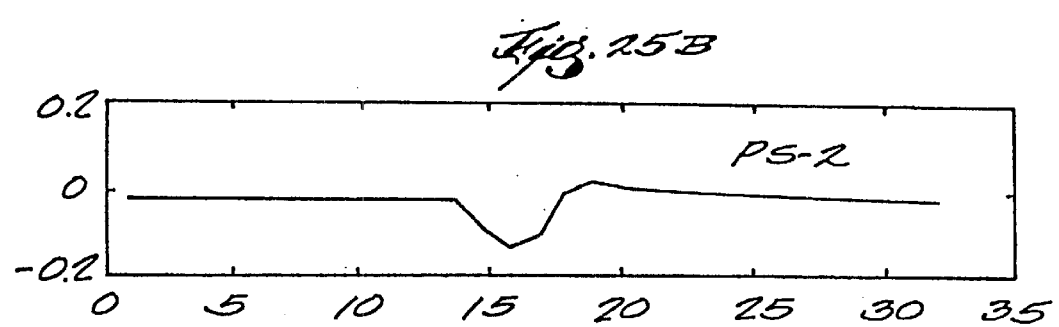
Figure 25C:
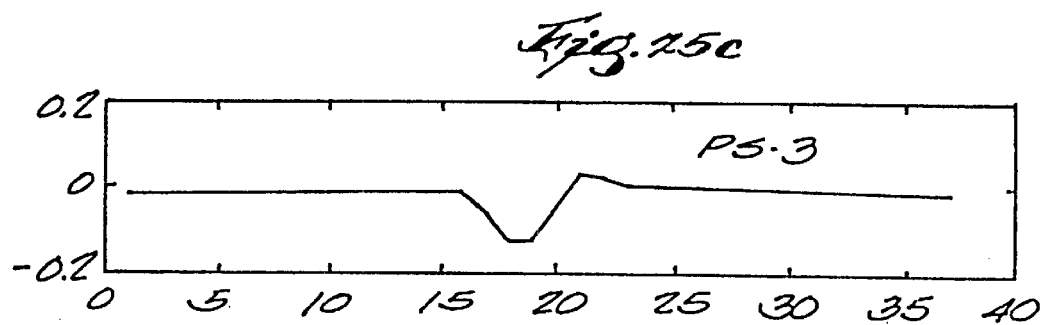
Figure 26A:
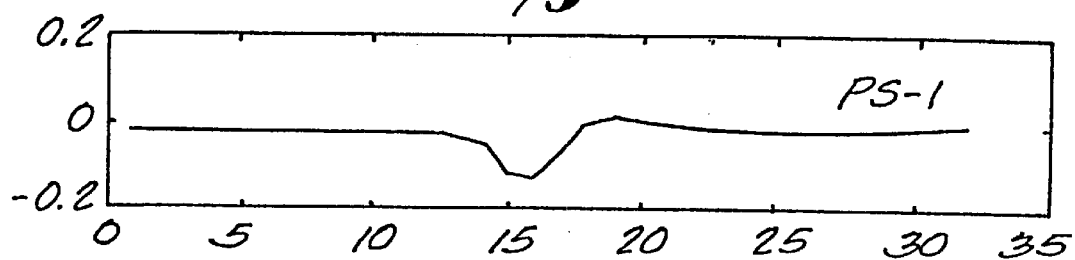
FIGS. 26A to C show the artifact signals of the three pacing artifacts shown in FIGS. 25A to C, after alignment and truncation.
Figure 26B:
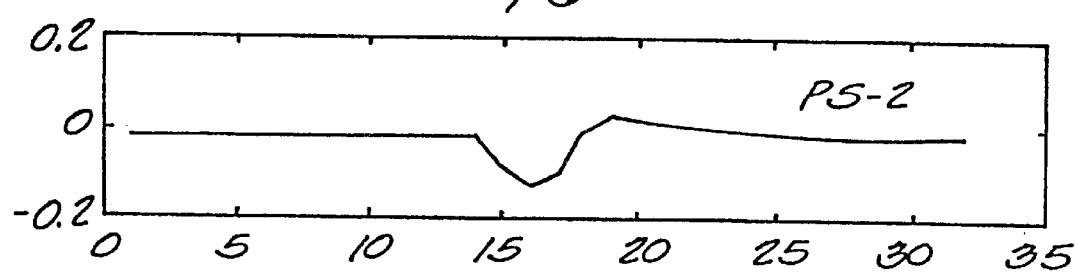
Figure 26C:
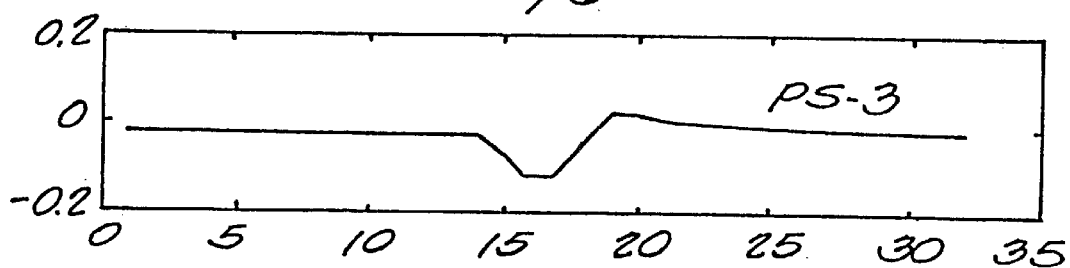

FIGS. 25A to C represent the signals PS-1; PS-2; and PS-3 contained by the three windows manually selected about the pacing pulses, respectively PA-1; PA-2; and PA-3. The physician manually aligns the three signals PS-1; PS-2; and PS-3 and truncates them at the same length, as FIGS. 26A to C show. In FIGS. 26A to C, the three signals PS-1; PS-2; and PS-3 have been aligned about their largest positive peak, although other alignment techniques could be used.

Figure 27:
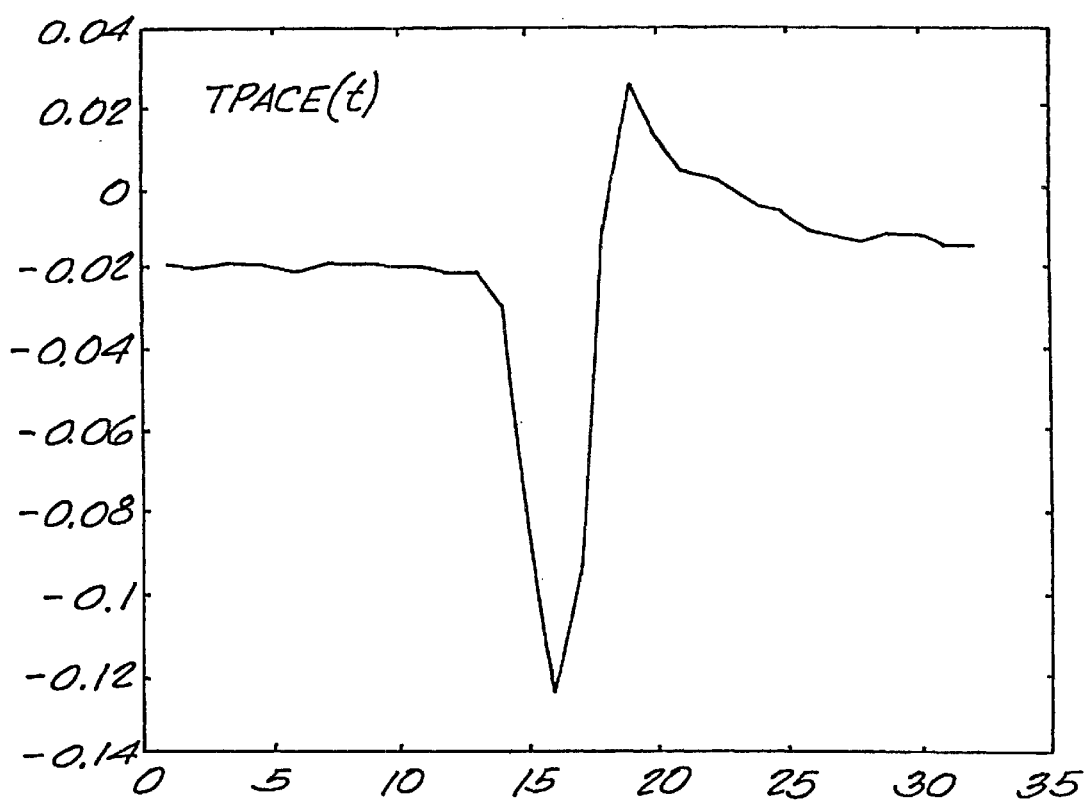
FIG. 27 shows the artifact template that results from averaging the three artifact signals shown in FIGS. 26A to C.
Figure 28A:
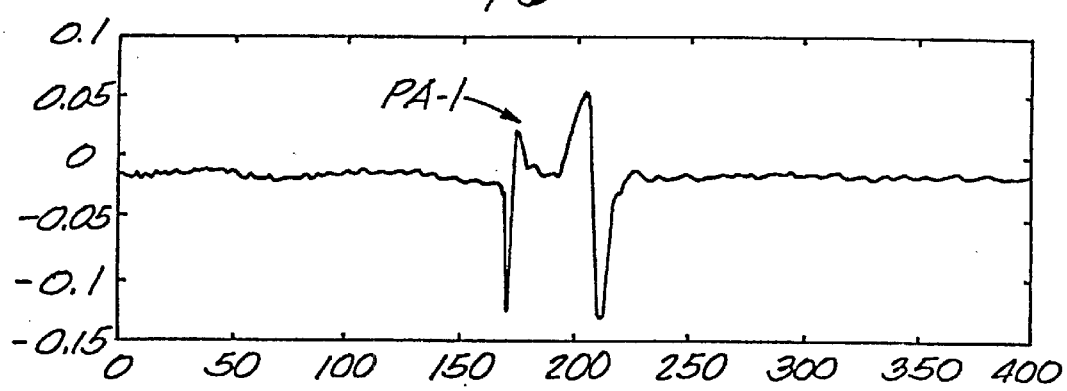
FIGS. 28A and B show the alignment of the first pacing artifact (in FIG. 28A) with the artifact template (in FIG. 28B).
Figure 28B:
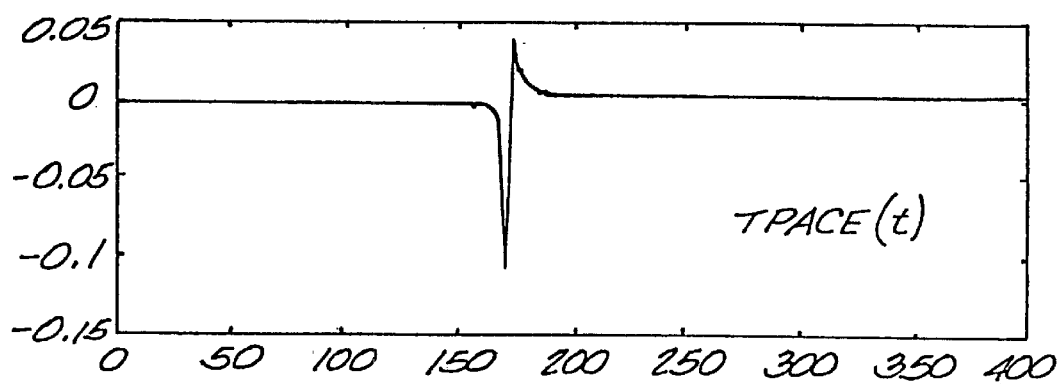

FIG. 27 shows the template TPACE(t) of the pacing artifact generated by averaging the three signals PS-1; PS-2; and PS-3 after alignment and truncation (i.e., the signals shown in FIGS. 26A to C are averaged). As FIGS. 28A and B show, the template TPACE(t) (FIG. 28B) is aligned with the first pacing pulse in the electrogram (FIG. 28A) prior to executing the adaptive algorithm for artifact removal.

It is not necessary to generate a new pacing artifact template TPACE(t) for the electrogram sensed by each electrode. The same initial template TPACE(t) from only one of the electrodes can be used for every electrogram. Alternatively, pacing signals from different electrodes can be aligned for averaging to create the template TPACE(t), which is then used for all electrograms.

The template TPACE(t) can also be generated by approximating the pacing pulse using suitable mathematical techniques, for example, spline interpolation. A universal template TPACE(t) can also be generated from recordings taken from different patients at different times with different equipment, although such different records may require proper adjustment before generating the universal template TPACE(t).

The filter 56 expresses the input signal with respect to time IN(t) in term of the function expressed as:

$$IN(t)=EG(t)+PACE(t)$$

where:

EG(t) is the actual electrogram, and

PACE(t) is the pacing artifact.

The template TPACE(t) of the filter 56 reduces IN(t), so the output signal EG(t) is expressed as IN (t)−TPACE(t). The filter 56 changes TPACE(t) over time based upon the energy of the output EG(t) so as to minimize the energy of (PACE(t)−TPACE(t)) over time, and therefore, the energy of EG(t).

Expressed differently, the filter 56 seeks to minimize the function EG(t)+PACE(t)−TPACE(t) over time. Ideally, the energy of EG(t) is minimized over time when TPACE(t) equals PACE(t), therefore being equal to the energy of EG(t).

The filter algorithm changes TPACE(t) over time applying known iterative techniques. For example, when applying the Least-Mean-Squares (LMS) technique, the template for TPACE(t) is used as a reference input for the LMS algorithm. The weight vector is initialized at [K00 . . . 0]. The variable K is chosen equal to the ratio between the peak of PACE(t) and the peak of the template TPACE(t). When PACE(t)=TPACE(t), k is equal to one. Further details of LMS are found in "Adaptive Filter Theory" by S. Haykin (Prentice Hall, 1991)

Other conventional iterative techniques like Recursive-Least-Squares or Steepest-Descent can also be used to achieve the same result.

EXAMPLE (Adaptive Filtering)

Figure 20A:
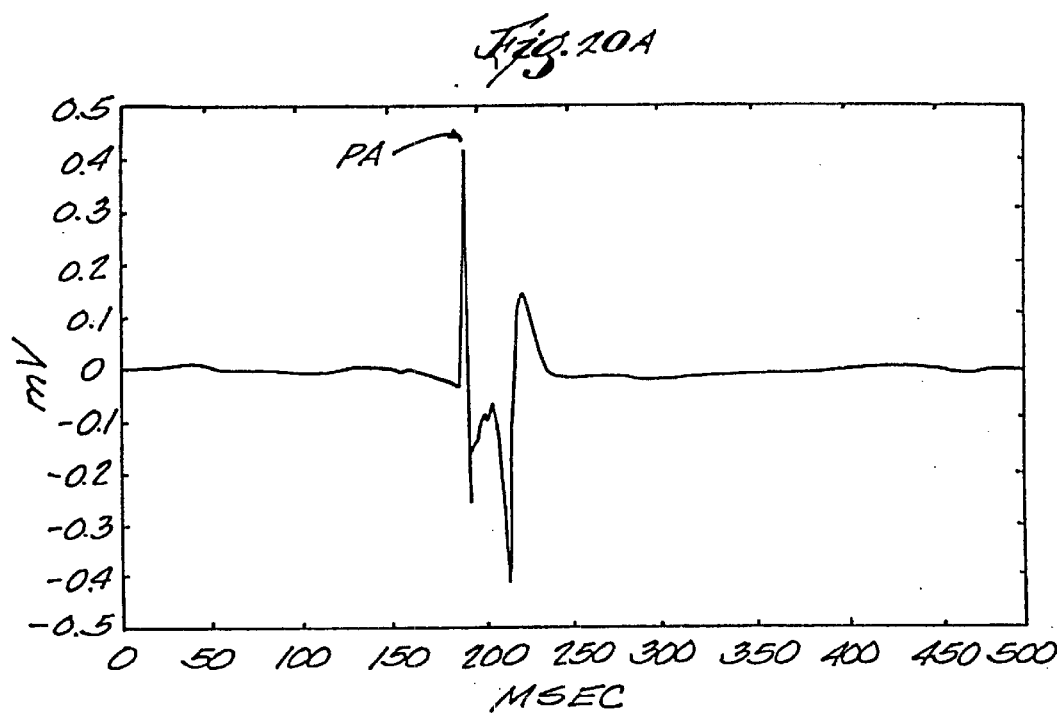
FIGS. 20A and 20B are representative electrogram morphologies processed by the adaptive filtering technique shown in FIG. 19 to remove a pacing artifact.
Figure 20B:
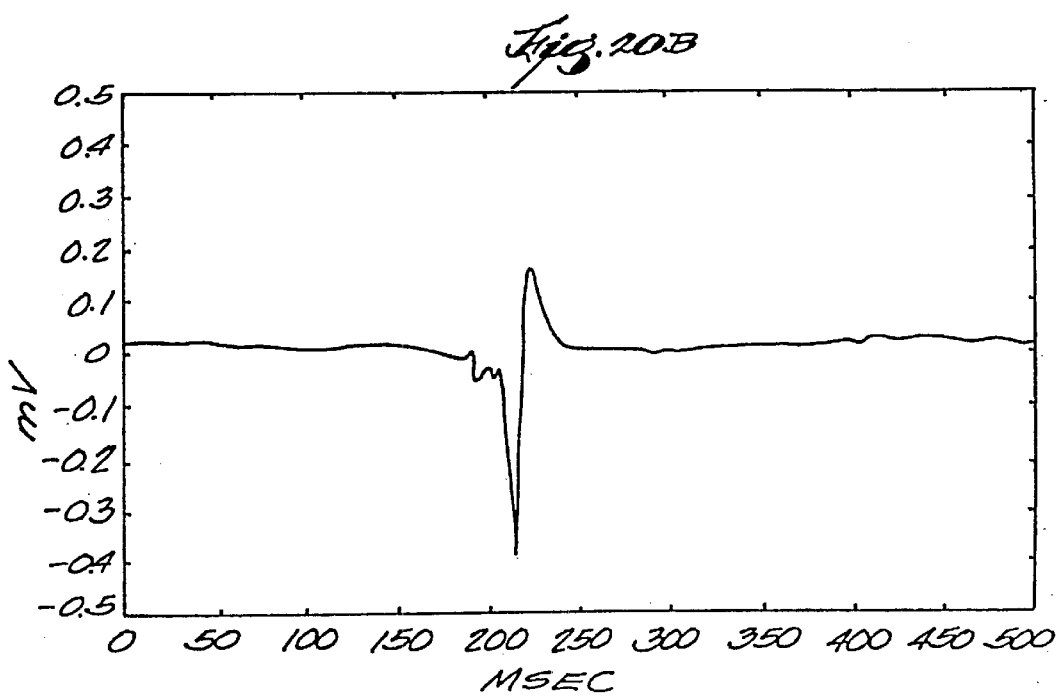

FIG. 20A shows a representative paced electrogram. The designation PA in FIG. 20A marks the location of the pacing artifact. FIG. 20B shows the paced electrogram after filtering using the LMS technique above described. FIG. 20B shows the effectiveness of the adaptive filter to remove the pacing artifact, without otherwise altering the morphology of the paced electrogram.

Either of the above described techniques for removing the pacing artifact have application outside the conditioning of the electrogram for morphology matching described herein. Either technique has application whenever it is desired to remove an artifact signal from a useful signal or to otherwise eliminate virtually any signal of a known shape. As a general proposition, nonlinear filtering or adaptive filtering, as above described, can be used whenever it is desired to remove cardiac related. or other periodic artifacts, for example, in respiratory signals, or EEG's, or from neurological signals. Nonlinear filtering or adaptive filtering, as above described, can also be used to eliminate periodic artifacts that are not cardiac related, for example, 50 to 60 Hz noise from sensed signals due to poor power source isolation.

In the presence of a pacing artifact, nonlinear filtering or adaptive filtering, as above described, can also be used to remove the pacing artifact before measuring the level of fractionation in an electrogram. Since a pacing artifact looks much like an electrogram, it is desirable to remove it before analyzing for actual fractionation.

As another example, nonlinear filtering or adaptive filtering, as above described, can be used to remove a pacing artifact when it is desired to conduct a frequency domain analysis of the cardiac signal, to determine the regularity of the heart beat.

Any portion of the electrogram can be isolated for elimination using the filtering techniques described above, not merely the pacing artifact. The nonlinear and adaptive filtering techniques can be used in applications where low pass filtering cannot be used. For example, while body surface mapping can use low pass filtering of electrograms, endocardial mapping cannot, due to the use of higher frequencies than in electrocardiograms. For example, a common electrocardiogram frequency spectrum is 0.05 to 100 Hz, whereas a common bipolar electrogram spectrum is 1 to 300 Hz.

Nonlinear filtering or adaptive filtered, as above described, can be used for processing or analyzing virtually any signal derived from a biological event. In addition to processing or analyzing signals derived from cardiac-related events, nonlinear filter or adaptive filtering can be used to process or analyze electroencephalograms, respiratory signals, electrogastrograms, and electromyograms.

Various features of the invention are set forth in the following claims.

We claim:

1. A system for acquiring and analyzing electrograms in myocardial tissue, comprising:

a member supporting multiple electrodes in a three dimensional, radially expanded array adapted to be in operative association with a region of heart tissue;

a first processing element including a pacing module and a signal processing module coupled to the multiple electrodes to acquire a sample of a cardiac event by placing the heart at a predetermined location while conditioning the multiple electrodes to sense paced electrograms occurring in the tissue region during pacing; and a second processing element including means for electronically comparing the sample to a template of a cardiac event of known diagnosis and generating an output based upon the comparison, whereby the output provides a diagnostic indicator based upon pacing.

2. A system according to claim 1, wherein the output comprises a matching factor indicating how alike the sample is to the template.

3. A system according to claim 2, further comprising a third processing element for comparing the matching factor to a predetermined value to identify a potential ablation site.

4. A system according to claim 1, wherein the second processing element compares the sample to the template by matched filtering.

5. A system according to claim 1, wherein the second processing element compares the sample to the template by cross correlation.

6. A system according to claim 1, wherein the processing element compares the sample to the template by deriving a norm of the difference.

7. A system according to claim 1, wherein the second processing element compares the sample to the template by using the template to create a matched filtered sample having a symmetry and by analyzing the symmetry of the matched filtered sample.

8. A system according to claim 1, wherein the sample and the template each comprises a plot of biopotentials over time and not a spacial distribution of endocardial surface activation.

9. A method for acquiring and analyzing electrograms in myocardial tissue, comprising:

deploying a three dimensional, radially expanded array of multiple electrodes in operative association with a region of heart tissue;

acquiring a sample of a cardiac event by placing the heart at a predetermined location using the multiple electrodes, while conditioning the multiple electrodes to sense paced electrograms occurring in the tissue region during pacing; and electronically comparing the sample to a template of a cardiac event of known diagnosis and generating an output based upon the comparison, whereby the output provides a diagnostic indicator based upon pacing.

10. A method according to claim 9, further including changing the predetermined location to pace the heart while conditioning the multiple electrodes to sense paced electrograms occurring as a result of pacing at different locations.

11. A method according to claim 9, wherein the comparing step provides an output comprising a matching factor indicating how alike the sample is to the template.

12. A method according to claim 11, including comparing the matching factor to a determined value to identify a potential ablation site.

13. A method according to claim 9, wherein the comparing step electronically compares the sample to the template by matched filtering.

14. A method according to claim 9, wherein the comparing step electronically compares the sample to the template by cross correlation.

15. A method according to claim 9, wherein the comparing step electronically compares the sample to the template by deriving a norm of the difference.

16. A method according to claim 9, wherein the comparing step compares the sample to the template by using the template to create a matched filtered sample having a symmetry and by analyzing the symmetry of the matched filtered sample.

17. The method of claim 9, wherein the sample and the template each comprises a plot of biopotentials over time and not a spacial distribution of endocardial surface activation.

* * * * *

Disclaimer 6,487,441—David K. Swanson, Mountain View; James G. Whayne, Saratoga; Dorin Panescu, Sunnyvale, all of CA. SYSTEMS AND METHODS FOR ACQUIRING AND ANALYZING ELECTROGRAMS IN MYOCARDIAL TISSUE. Patent dated November 26, 2002. Disclaimer filed December 2, 2002, by the assignee, EP Technologies, Inc.

The term of this patent shall not extend beyond the expiration date of Pat. No. 5,954,662.

*(Official Gazette, July 15, 2003)*